(12) United States Patent
Clawson

(10) Patent No.: US 10,699,548 B2
(45) Date of Patent: Jun. 30, 2020

(54) EXPEDITED DISPATCH PROTOCOL SYSTEM AND METHOD

(71) Applicant: Jeffrey J. Clawson, Holladay, UT (US)

(72) Inventor: Jeffrey J. Clawson, Holladay, UT (US)

(*) Notice: Subject to any disclaimer, the term of this patent is extended or adjusted under 35 U.S.C. 154(b) by 0 days.

(21) Appl. No.: 16/389,610

(22) Filed: Apr. 19, 2019

(65) Prior Publication Data
US 2019/0325726 A1    Oct. 24, 2019

Related U.S. Application Data

(60) Provisional application No. 62/659,947, filed on Apr. 19, 2018.

(51) Int. Cl.
| G08B 21/02 | (2006.01) |
| H04W 4/90 | (2018.01) |
| H04M 3/51 | (2006.01) |
| G08B 25/00 | (2006.01) |
| G16H 10/60 | (2018.01) |

(52) U.S. Cl.
CPC ......... G08B 21/02 (2013.01); G08B 25/006 (2013.01); G16H 10/60 (2018.01); H04M 3/5116 (2013.01); H04W 4/90 (2018.02)

(58) Field of Classification Search
CPC ...... G08B 21/02; G08B 25/006; G16H 10/60; H04W 4/90; H04M 3/5116; H04M 2242/04; G06F 3/0484
USPC .............. 340/286.06, 286.07, 539.1, 539.11, 340/539.12, 573.1; 379/37, 45; 600/300, 600/301; 715/700, 741
See application file for complete search history.

(56) References Cited

U.S. PATENT DOCUMENTS

| 3,799,147 A | 3/1974 | Adolph et al. |
| 4,130,881 A | 12/1978 | Haessler et al. |
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Lamb et al. |

(Continued)

FOREIGN PATENT DOCUMENTS

| CN | 1674685 A | 9/2005 |
| CN | 101169840 A | 4/2008 |

(Continued)

OTHER PUBLICATIONS

U.S. Appl. No. 14/757,797, Non-Final Office Action, dated Aug. 29, 2019, 20 pages.

(Continued)

*Primary Examiner* — Hung T Nguyen
(74) *Attorney, Agent, or Firm* — Stoel Rives LLP

(57) ABSTRACT

A dispatch center utilizes an expedited dispatch protocol for an information provider who is a trained first responder to communicate with the dispatch center and provide patient information with little or no prompting from a dispatcher. The expedited dispatch protocol provides expedited processing of the patient information and generates a determinant code which indicates the priority of the emergency. The expedited dispatch protocol provides a uniform, consistent result to objectively select priority and generate an appropriate emergency response.

26 Claims, 59 Drawing Sheets

(56) References Cited

U.S. PATENT DOCUMENTS

| | | |
|---|---|---|
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |
| 5,072,383 A | 12/1991 | Brimm et al. |
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |
| 5,193,855 A | 3/1993 | Shamos |
| 5,228,449 A | 7/1993 | Christ et al. |
| 5,253,164 A | 10/1993 | Holloway et al. |
| 5,255,187 A | 10/1993 | Sorensen |
| 5,291,399 A | 3/1994 | Chaco |
| 5,323,444 A | 6/1994 | Ertz et al. |
| 5,339,351 A | 8/1994 | Hoskinson et al. |
| 5,348,008 A | 9/1994 | Bomn et al. |
| 5,379,337 A | 1/1995 | Castillo et al. |
| 5,404,292 A | 4/1995 | Hendrickson |
| 5,410,471 A | 4/1995 | Alyfuku et al. |
| 5,423,061 A | 6/1995 | Fumarolo et al. |
| 5,438,996 A | 8/1995 | Kemper et al. |
| 5,441,047 A | 8/1995 | David |
| 5,462,051 A | 10/1995 | Oka |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,536,084 A | 7/1996 | Curtis et al. |
| 5,544,649 A | 8/1996 | David et al. |
| 5,554,031 A | 9/1996 | Moir et al. |
| 5,590,269 A | 12/1996 | Kruse et al. |
| 5,593,426 A | 1/1997 | Morgan et al. |
| 5,594,638 A | 1/1997 | Iliff |
| 5,594,786 A | 1/1997 | Chaco et al. |
| 5,596,994 A | 1/1997 | Bro |
| 5,630,125 A | 5/1997 | Zellweger |
| 5,636,873 A | 6/1997 | Sonsteby |
| 5,650,995 A | 7/1997 | Kent |
| 5,660,176 A | 8/1997 | Iliff |
| 5,675,372 A | 10/1997 | Aguayo, Jr. et al. |
| 5,682,419 A | 10/1997 | Grube et al. |
| 5,684,860 A | 11/1997 | Milani et al. |
| 5,689,229 A | 11/1997 | Chaco et al. |
| 5,719,918 A | 2/1998 | Serbetciouglu et al. |
| 5,722,418 A | 3/1998 | Bro |
| 5,724,983 A | 3/1998 | Selker et al. |
| 5,734,706 A | 3/1998 | Windsor et al. |
| 5,745,532 A | 4/1998 | Campana, Jr. |
| 5,748,907 A | 5/1998 | Crane |
| 5,754,960 A | 5/1998 | Downs et al. |
| 5,759,044 A | 6/1998 | Redmond |
| 5,761,278 A | 6/1998 | Pickett et al. |
| 5,761,493 A | 6/1998 | Blakeley et al. |
| 5,764,923 A | 6/1998 | Tallman et al. |
| 5,787,429 A | 7/1998 | Nikolin, Jr. et al. |
| 5,805,670 A | 9/1998 | Pons et al. |
| 5,809,493 A | 9/1998 | Anamed et al. |
| 5,822,544 A | 10/1998 | Chaco et al. |
| 5,823,948 A | 10/1998 | Ross, Jr. et al. |
| 5,826,077 A | 10/1998 | Blakeley et al. |
| 5,832,187 A | 11/1998 | Pedersen et al. |
| 5,842,173 A | 11/1998 | Strum et al. |
| 5,844,817 A | 12/1998 | Lobley et al. |
| 5,850,611 A | 12/1998 | Krebs |
| 5,857,966 A | 1/1999 | Clawson |
| 5,901,214 A | 5/1999 | Shaffer et al. |
| 5,902,234 A | 5/1999 | Webb |
| 5,910,987 A | 6/1999 | Ginter |
| 5,912,818 A | 6/1999 | McGrady et al. |
| 5,915,019 A | 6/1999 | Ginter et al. |
| 5,926,526 A | 7/1999 | Rapaport et al. |
| 5,933,780 A | 8/1999 | Connor et al. |
| 5,961,446 A | 10/1999 | Beller et al. |
| 5,962,891 A | 10/1999 | Arai |
| 5,964,700 A | 10/1999 | Tallman et al. |
| 5,986,543 A | 11/1999 | Johnson |
| 5,989,187 A | 11/1999 | Clawson |
| 5,991,730 A | 11/1999 | Lubin et al. |
| 5,991,751 A | 11/1999 | Rivette et al. |
| 6,004,266 A | 12/1999 | Clawson |
| 6,010,451 A | 1/2000 | Clawson |
| 6,022,315 A | 2/2000 | Iliff |
| 6,035,187 A | 3/2000 | Franza |
| 6,040,770 A | 3/2000 | Britton |
| 6,052,574 A | 4/2000 | Smith, Jr. |
| 6,053,864 A | 4/2000 | Clawson |
| 6,058,179 A | 5/2000 | Shaffer et al. |
| 6,074,345 A | 6/2000 | Van Oostrom et al. |
| 6,076,065 A | 6/2000 | Clawson |
| 6,078,894 A | 6/2000 | Clawson et al. |
| 6,084,510 A | 7/2000 | Lemelson et al. |
| 6,106,459 A | 8/2000 | Clawson |
| 6,112,083 A | 8/2000 | Sweet et al. |
| 6,115,646 A | 9/2000 | Fiszman et al. |
| 6,117,073 A | 9/2000 | Jones et al. |
| 6,118,866 A | 9/2000 | Shtivelman |
| 6,127,975 A | 10/2000 | Maloney |
| 6,134,105 A | 10/2000 | Lueker |
| 6,292,542 B1 | 9/2001 | Bilder |
| 6,370,234 B1 | 4/2002 | Kroll |
| 6,535,121 B2 | 3/2003 | Matheny |
| 6,594,634 B1 | 7/2003 | Hampton et al. |
| 6,607,481 B1 | 8/2003 | Clawson |
| 6,610,012 B2 | 8/2003 | Mault |
| 6,696,956 B1 | 2/2004 | Uchida et al. |
| 6,710,711 B2 | 3/2004 | Berry |
| 6,771,163 B2 | 8/2004 | Linnett et al. |
| 6,879,819 B2 | 4/2005 | Brooks |
| 6,901,397 B1 | 5/2005 | Moldenhauer et al. |
| 6,931,112 B1 | 8/2005 | McFarland et al. |
| 6,968,375 B1 | 11/2005 | Brown |
| 7,043,262 B2 | 5/2006 | Nageli |
| 7,106,835 B2 | 9/2006 | Saalsaa |
| 7,194,395 B2 | 3/2007 | Genovese |
| 7,289,944 B1 | 10/2007 | Genovese |
| 7,428,301 B1 | 9/2008 | Clawson |
| 7,436,937 B2 | 10/2008 | Clawson |
| 7,438,301 B2 | 10/2008 | Schilling et al. |
| 7,645,234 B2 | 1/2010 | Clawson |
| 7,703,020 B2 | 4/2010 | Bhattaru |
| 7,783,586 B2 | 8/2010 | Friedlander et al. |
| 7,978,826 B2 | 7/2011 | Salafia et al. |
| 8,066,638 B2 | 11/2011 | Clawson |
| 8,081,951 B1 | 12/2011 | Blum |
| 8,103,523 B2 | 1/2012 | Clawson |
| 8,294,570 B2 | 10/2012 | Clawson |
| 8,335,298 B2 | 12/2012 | Clawson |
| 8,346,942 B2 | 1/2013 | Ezerzer et al. |
| 8,355,483 B2 | 1/2013 | Clawson |
| 8,396,191 B2 | 3/2013 | Clawson |
| 8,417,533 B2 | 4/2013 | Clawson |
| 8,462,914 B2 | 6/2013 | Ragno et al. |
| 8,488,748 B2 | 7/2013 | Clawson |
| 8,494,868 B2 | 7/2013 | Saalsaa |
| 8,538,374 B1 | 9/2013 | Haimo et al. |
| 8,670,526 B2 | 3/2014 | Clawson |
| 8,712,020 B2 | 4/2014 | Clawson |
| 8,873,719 B2 | 10/2014 | Clawson |
| 8,971,501 B2 | 3/2015 | Jeffrey |
| 9,319,859 B2 | 4/2016 | Clawson |
| 9,875,514 B2 | 1/2018 | Smallwood |
| 9,877,171 B2 | 1/2018 | Clawson |
| 2002/0004729 A1 | 1/2002 | Zak et al. |
| 2002/0022492 A1 | 2/2002 | Barak et al. |
| 2002/0106059 A1 | 8/2002 | Kroll et al. |

(56) References Cited

U.S. PATENT DOCUMENTS

| | | |
|---|---|---|
| 2003/0025602 A1* | 2/2003 | Medema .............. H04W 64/00 340/568.1 |
| 2003/0028536 A1 | 2/2003 | Singh et al. |
| 2003/0050538 A1 | 3/2003 | Naghavi et al. |
| 2003/0179862 A1 | 9/2003 | Sierra et al. |
| 2003/0187615 A1 | 10/2003 | Epler |
| 2003/0195394 A1 | 10/2003 | Saalsaa |
| 2003/0211856 A1 | 11/2003 | Zilliacus |
| 2003/0212575 A1 | 11/2003 | Saalsaa et al. |
| 2004/0219927 A1 | 11/2004 | Sumner |
| 2005/0015115 A1 | 1/2005 | Sullivan et al. |
| 2005/0065813 A1 | 3/2005 | Mishelevich et al. |
| 2006/0031097 A1 | 2/2006 | Lipscher |
| 2006/0038674 A1 | 2/2006 | Sumcad et al. |
| 2006/0059423 A1 | 3/2006 | Lehmann et al. |
| 2006/0122520 A1 | 6/2006 | Banet et al. |
| 2006/0152372 A1 | 7/2006 | Stout |
| 2006/0167346 A1 | 7/2006 | Sarel |
| 2006/0173500 A1 | 8/2006 | Walker et al. |
| 2006/0178908 A1 | 8/2006 | Rappaport |
| 2006/0212315 A1 | 9/2006 | Wiggins |
| 2006/0225213 A1 | 10/2006 | Tomcany |
| 2007/0055559 A1 | 3/2007 | Clawson |
| 2007/0111702 A1 | 5/2007 | Sanzelius et al. |
| 2007/0112275 A1 | 5/2007 | Cooke et al. |
| 2007/0116189 A1 | 5/2007 | Clawson |
| 2007/0189480 A1 | 8/2007 | Salafia et al. |
| 2007/0201664 A1 | 8/2007 | Salafia et al. |
| 2008/0208801 A1 | 8/2008 | Friedlander et al. |
| 2008/0310600 A1 | 12/2008 | Clawson |
| 2009/0037374 A1 | 2/2009 | Delia et al. |
| 2009/0067585 A1 | 3/2009 | Clawson |
| 2009/0168975 A1 | 7/2009 | Clawson |
| 2009/0179756 A1 | 7/2009 | Stout |
| 2009/0191529 A1 | 7/2009 | Mozingo et al. |
| 2009/0233631 A1 | 9/2009 | Butler, Sr. et al. |
| 2009/0276489 A1 | 11/2009 | Ragno et al. |
| 2010/0004710 A1 | 1/2010 | Kellum |
| 2010/0088135 A1 | 4/2010 | Nielsen et al. |
| 2010/0121156 A1 | 5/2010 | Yoo |
| 2010/0152800 A1 | 6/2010 | Walker et al. |
| 2010/0198755 A1 | 8/2010 | Soll et al. |
| 2010/0257250 A1 | 10/2010 | Salafia et al. |
| 2011/0050417 A1 | 3/2011 | Piccioni |
| 2011/0064204 A1 | 3/2011 | Clawson |
| 2011/0066002 A1 | 3/2011 | Clawson |
| 2011/0099031 A1 | 4/2011 | Nair |
| 2011/0205052 A1 | 8/2011 | Clawson |
| 2011/0215930 A1 | 9/2011 | Lee |
| 2012/0034897 A1 | 2/2012 | Kreitzer et al. |
| 2012/0066345 A1 | 3/2012 | Rayan et al. |
| 2012/0171989 A1 | 7/2012 | Matsuo et al. |
| 2012/0183128 A1 | 7/2012 | Clawson |
| 2012/0207286 A1 | 8/2012 | Clawson |
| 2012/0210271 A1 | 8/2012 | Clawson |
| 2013/0100268 A1 | 4/2013 | Mihailidis et al. |
| 2014/0031885 A1 | 1/2014 | Elghazzawi et al. |
| 2014/0064462 A1 | 3/2014 | Clawson |
| 2014/0211927 A1 | 7/2014 | Clawson |
| 2014/0213212 A1 | 7/2014 | Clawson |
| 2014/0243749 A1 | 8/2014 | Edwards et al. |
| 2015/0289121 A1 | 10/2015 | Lesage et al. |
| 2015/0289122 A1 | 10/2015 | Friesen |
| 2016/0088455 A1 | 3/2016 | Bozik et al. |
| 2016/0148490 A1 | 5/2016 | Barnes et al. |
| 2016/0212605 A1 | 7/2016 | Clawson |
| 2016/0302050 A1 | 10/2016 | Blando et al. |
| 2016/0309026 A1 | 10/2016 | Sterman |
| 2016/0352898 A1 | 12/2016 | Clawson |
| 2017/0028767 A1 | 2/2017 | Tiberius |
| 2017/0187878 A1 | 6/2017 | Clawson |
| 2017/0262614 A1 | 9/2017 | Vishnubhatla et al. |
| 2017/0295477 A1 | 10/2017 | Clawson |
| 2018/0053401 A1 | 2/2018 | Martin et al. |
| 2019/0313230 A1* | 10/2019 | MacGabann .......... H04W 4/023 |
| 2019/0318290 A1 | 10/2019 | Clawson et al. |
| 2019/0378397 A1* | 12/2019 | Williams, II .......... G06N 20/00 |

FOREIGN PATENT DOCUMENTS

| | | |
|---|---|---|
| CN | 201117055 Y | 9/2008 |
| CN | 102714524 A | 10/2012 |
| EP | 2476092 A1 | 3/2011 |
| GB | 2471960 | 1/2011 |
| GB | 2478171 A | 8/2011 |
| GB | 2482741 A | 2/2012 |
| GB | 2489875 A | 10/2012 |
| JP | 2002049693 | 2/2002 |
| JP | 2003109162 A | 4/2003 |
| JP | 2003111735 | 4/2003 |
| JP | 2003187003 A | 7/2003 |
| JP | 2003256963 A | 12/2003 |
| JP | 2010033201 A | 12/2010 |
| KR | 1020050085778 | 8/2005 |
| KR | 1020060084866 | 7/2006 |
| KR | 20070043337 A | 4/2007 |
| KR | 1020080004125 | 1/2008 |
| KR | 1020090014837 A | 2/2009 |
| WO | 2004030259 | 4/2004 |
| WO | 2005039406 A1 | 5/2005 |
| WO | 2006015229 A2 | 2/2006 |
| WO | 2007121237 | 10/2007 |
| WO | 2008014398 A2 | 1/2008 |
| WO | 2008156876 A1 | 12/2008 |
| WO | 2010101580 | 9/2010 |
| WO | 2010120321 | 10/2010 |
| WO | 2011031382 | 3/2011 |
| WO | 2011031383 | 3/2011 |
| WO | 2011106036 | 9/2011 |
| WO | 2012100052 | 7/2012 |
| WO | 2012108897 | 8/2012 |
| WO | 2012108898 A1 | 8/2012 |
| WO | 2014039228 | 3/2014 |
| WO | 2014120428 | 8/2014 |
| WO | 2014121010 | 8/2014 |
| WO | 2016109855 | 7/2016 |
| WO | 2016190962 | 12/2016 |
| WO | 2017112392 | 6/2017 |
| WO | 2017176417 | 10/2017 |
| WO | 2019200019 | 10/2019 |
| WO | 2019204746 | 10/2019 |

OTHER PUBLICATIONS

U.S. Appl. No. 15/083,810, Notice of Allowance, dated Sep. 23, 2016, 14 pages.
U.S. Appl. No. 15/083,810, Non-Final Office Action, dated Jul. 15, 2016, 28 pages.
U.S. Appl. No. 15/094,424, Advisory Action, dated Oct. 16, 2017, 4 pages.
U.S. Appl. No. 15/094,424, Final Office Action, dated Sep. 5, 2017, 35 pages.
U.S. Appl. No. 15/094,424, Notice of Allowance, dated Feb. 23, 2018, 5 pages.
U.S. Appl. No. 15/094,424, Non-Final Office Action, dated May 31, 2017, 68 pages.
Anonymous, "Suburban Chicago towns centralize 911 services", Communications News, v31 n10, Oct. 1994, 2 pages.
Best, Wendy, "999 United Emergency services share life-saving Role to boost response", Western Daily Press, WOP Severnside ed., May 27, 1999, 2 pages.
CBS web page News Story, "911 Operator: 'It's got to be Hell (excerpts from 911 operators' actions during the attacks on Sep. 11, 2001)", Mar. 31, 2006, 3 pages.
Clark University, "Active Shooter Emergency Plan", Jan. 11, 2013, 11 pages.
Clark, Mark, "Learning from CAD System Implementation", Communications, v29 n8, Aug. 1992, 5 pages.
Esch, Trevor, "Geac Completes Software Install", Wireless Week, Nov. 18, 1996, 3 pages.

(56) References Cited

OTHER PUBLICATIONS

Harris, Roger, "Updated 911 Phone System Top Concern of Residents", Business First-Louisville, v9 n19 s1, Dec. 1992, 3 pages.
Holroyd, Brian, et al., "Medical Control; Quality Assurance in Prehospital Care", JAMA, the Journal of American Medical Association, v256, n8, Aug. 1986, pp. 1027-1031.
Jamb Innovations, LLC, uBurn, https://web.archive.org/web/20120506154615/https://itunes.apple.com/us/app/uburn/id327057175?mt=8, May 6, 2012, 2 pages.
Kothari, R.U., et al., "Cincinnati Prehospital Stroke Scale: Reproducibility and Validity", Annals of Emergency Medicine, 33/3, https://www.ncbi.nlm.nih.gov/pubmed/10092713, Apr. 30, 1999, pp. 373-378.
Liferidge, Aisha T., et al., "Ability of Laypersons to Use the Cincinnati Prehospital Stroke Scale", Prehospital Emergency Care, Elsevier, vol. 8, No. 4, Oct. 1, 2004, pp. 384-387.
Nor, A. Mohd et al., "Agreement Between Ambulance Paramedic-and Physician-Recorded Neurological Signs With Face Arm Speech Test (FAST) in Acute Stroke Patients", http://stroke.ahajournals.org/content/35/6/1355, visited Nov. 17, 2013, Apr. 29, 2004, 3 pages.
Nordberg, Marie, "Dispatch Disasters", Emergency Medicine, Aug. 1995, 10 pages.
PCT/US2008/054987, International Search Report, dated Oct. 8, 2008, 2 pages.
PCT/US2008/054987, Written Opinion, dated Oct. 8, 2008, 9 pages.
PCT/US2009/040909, International Search Report and Written Opinion, dated Jun. 10, 2009, 10 pages.
PCT/US2009/048577, International Preliminary Report of Patentability, dated Oct. 27, 2011, 7 pages.
PCT/US2009/048577, International Search Report and Written Opinion, dated Aug. 7, 2009, 9 pages.
PCT/US2010/043308, International Search Report and Written Opinion, dated Jan. 19, 2011, 9 pages.
PCT/US2010/043308, International Preliminary Report of Patentability, dated Mar. 22, 2012, 6 pages.
PCT/US2010/043311, International Preliminary Report of Patentability, dated Mar. 29, 2012, 6 pages.
PCT/US2010/043311, International Search Report and Written Opinion, dated Jan. 19, 2011, 3 pages.
PCT/US2010/050402, International Search Report and Written Opinion, dated Apr. 27, 2011, 9 pages.
PCT/US2011/042543, International Search Report and Written Opinion, dated Feb. 9, 2012, 11 pages.
PCT/US2011/042543, International Preliminary Report of Patentability, dated Aug. 22, 2013, 7 pages.
PCT/US2011/042582, International Preliminary Report of Patentability, dated Aug. 22, 2013, 5 pages.
PCT/US2011/042582, International Search Report and Written Opinion, dated Feb. 9, 2012, 8 pages.
PCT/US2012/021867, International Search Report and Written Opinion, dated Aug. 30, 2012, 8 pages.
PCT/US2013/055537, International Search Report and Written Opinion, dated Nov. 22, 2013, 10 pages.
PCT/US2013/055537, International Preliminary Report of Patentability, dated Mar. 19, 2015, 33 pages.
PCT/US2014/011405, International Search Report and Written Opinion, dated Apr. 25, 2014, 10 pages.
PCT/US2014/014029, International Search Report and Written Opinion, dated May 16, 2014, 12 pages.
PCT/US2016/064719, International Search Report and Written Opinion, dated Feb. 16, 2017, 16 pages.
PCT/US2016/064719, International Preliminary Report of Patentability, dated Jul. 5, 2018, 11 pages.
PCT/US2017/021519, International Search Report and Written Opinion, dated May 22, 2017, 17 pages.
Peck, "Got a Minute? You Could Diagnose a Stroke", WebMD Health News, http://www.webmd.com/stroke/news/20030213/got-minute-you-could-diagnose-stroke, Feb. 13, 2003, 3 pages.
Poellmitz, William C., et al., "Wireless technology keeps public safety a step ahead", Nation's Cities Weekly, v21 n17, Apr. 27, 1998, 3 pages.
Qamar, Robert, "Dictaphone introduces Windows-based Computer-Aided Dispatch (CAD) system", Business Wire, (in commercial use in 1995), Apr. 23, 1996, 2 pages.
Radosevich, Lynda, "Network holds sway on life, death", Computerworld, v27 n21, May 24, 1993, 2 pages.
U.S. Appl. No. 09/685,697, Non-Final Office Action, dated Apr. 10, 2007, 9 pages.
U.S. Appl. No. 09/685,697, Final Office Action, dated Feb. 3, 2004, 5 pages.
U.S. Appl. No. 09/685,697, Non-Final Office Action, dated Jan. 4, 2005, 5 pages.
U.S. Appl. No. 09/685,697, Non-Final Office Action, dated Jul. 18, 2003, 8 pages.
U.S. Appl. No. 09/685,697, Non-Final Office Action, dated Jun. 26, 2006, 8 pages.
U.S. Appl. No. 09/685,697, Advisory Action, dated Mar. 13, 2006, 4 pages.
U.S. Appl. No. 09/685,697, Final Office Action, dated Oct. 4, 2005, 7 pages.
U.S. Appl. No. 09/685,697, Final Office Action, dated Oct. 9, 2007, 11 pages.
U.S. Appl. No. 10/140,635, Non-Final Office Action, dated Apr. 19, 2005, 11 pages.
U.S. Appl. No. 10/140,635, Final Office Action, dated Jan. 17, 2006, 13 pages.
U.S. Appl. No. 10/140,635, Final Office Action, dated Jul. 16, 2004, 11 pages.
U.S. Appl. No. 10/140,635, Final Office Action, dated Jun. 21, 2007, 15 pages.
U.S. Appl. No. 10/140,635, Non-Final Office Action, dated Oct. 3, 2003, 9 pages.
U.S. Appl. No. 10/140,635, Non-Final Office Action, dated Sep. 20, 2006, 15 pages.
U.S. Appl. No. 10/255,901, Non-Final Office Action, dated Jun. 7, 2006, 8 pages.
U.S. Appl. No. 10/255,905, Advisory Action, dated Aug. 11, 2006, 3 pages.
U.S. Appl. No. 10/255,901, Non-Final Office Action, dated Dec. 31, 2003, 8 pages.
U.S. Appl. No. 10/255,901, Advisory Action, dated Feb. 14, 2006, 3 pages.
U.S. Appl. No. 10/255,901, Notice of Allowance, dated Feb. 20, 2013, 9 pages.
U.S. Appl. No. 10/255,901, Final Office Action, dated Feb. 27, 2007, 8 pages.
U.S. Appl. No. 10/255,901, Final Office Action, dated Jun. 29, 2005, 7 pages.
U.S. Appl. No. 10/255,901, Final Office Action, dated Oct. 13, 2004, 8 pages.
U.S. Appl. No. 10/255,901, Non-Final Office Action, dated Sep. 6, 2007, 9 pages.
U.S. Appl. No. 10/255,905, Final Office Action, dated Feb. 9, 2006, 8 pages.
U.S. Appl. No. 10/255,905, Non-Final Office Action, dated Jan. 30, 2007, 7 pages.
U.S. Appl. No. 10/255,905, Notice of Non-Compliant Amendment, dated Jul. 9, 2007, 4 pages.
U.S. Appl. No. 10/255,905, Non-Final Office Action, dated May 19, 2004, 7 pages.
U.S. Appl. No. 10/255,905, Non-Final Office Action, dated May 26, 2005, 5 pages.
U.S. Appl. No. 10/255,905, Final Office Action, dated Oct. 5, 2007, 7 pages.
U.S. Appl. No. 12/268,963, Non-Final Office Action, dated Jul. 29, 2011, 18 pages.
U.S. Appl. No. 12/396,201, Non-Final Office Action, dated Mar. 8, 2011, 23 pages.
U.S. Appl. No. 12/422,561, Notice of Allowance, dated Dec. 9, 2014, 12 pages.

(56) References Cited

OTHER PUBLICATIONS

U.S. Appl. No. 12/422,561, Final Office Action, dated Feb. 1, 2013, 26 pages.
U.S. Appl. No. 12/422,561, Non-Final Office Action, dated Jul. 3, 2012, 21 pages.
U.S. Appl. No. 12/558,045, Non-Final Office Action, dated Mar. 22, 2012, 9 pages.
U.S. Appl. No. 12/558,808, Non-Final Office Action, dated Apr. 23, 2012, 9 pages.
U.S. Appl. No. 13/026,043, Notice of Allowance, dated Jan. 13, 2014, 9 pages.
U.S. Appl. No. 13/026,043, Non-Final Office Action, dated Oct. 10, 2013, 27 pages.
U.S. Appl. No. 13/026,055, Notice of Allowance, dated Jan. 24, 2013, 27 pages.
U.S. Appl. No. 13/354,116, Non-Final Office Action, dated Jan. 22, 2013, 9 pages.
U.S. Appl. No. 13/354,116, Notice of Allowance, dated Jun. 7, 2013, 7 pages.
U.S. Appl. No. 13/605,501, Notice of Allowance, dated Mar. 6, 2014, 7 pages.
U.S. Appl. No. 13/605,501, Non-Final Office Action, dated Nov. 18, 2013, 29 pages.
U.S. Appl. No. 13/755,793, Non-Final Office Action, dated Jul. 21, 2014, 17 pages.
U.S. Appl. No. 13/755,793, Notice of Allowance, dated Sep. 22, 2014.
U.S. Appl. No. 14/169,302, Notice of Allowance, dated Mar. 4, 2016, 13 pages.
U.S. Appl. No. 14/169,302, Non-Final Office Action, dated Sep. 25, 2015, 46 pages.
U.S. Appl. No. 14/723,947, Non-Final Office Action, dated Mar. 31, 2016, 33 pages.
U.S. Appl. No. 14/723,947, Notice of Allowance, dated Oct. 24, 2016, 29 pages.
U.S. Appl. No. 14/757,797, Final Office Action, dated Aug. 30, 2018, 25 pages.
U.S. Appl. No. 14/757,797, Notice of Allowance, dated Mar. 30, 2020, 12 pages.
Associated Press, "The Simpson Murder Case: Nicole Simpson's 911 Calls", The Los Angeles Times, Jun. 23, 1994, 8 pages.
Hawai'i Police Department, "Proper Use of 911", https://www.hawaiipolice.com/dispatch-911, Feb. 6, 2015, 1 pages.

\* cited by examiner

300

Paramount for Medical

File  View  Spec Logs  Options  Go to Language  Tabs  Version  About ProQA

6:36

| Entry | KQ | PDI/CEI | DLS | Summary |

Case Entry | Additional Information

| | |
|---|---|
| Location is: | 302 |
| Phone number is: | 304 |
| Caller's problem description is: | 306 |
| With patient now: | Yes           308 |
| Number of hurt/sick is: | 1              310 |
| Patient's age is: | 45    312    year(s) |
| Patient's gender is: | Male          314 |
| Is he awake (conscious)? | Yes           316 |
| Is he breathing? | No            318 |
| Chief Complaint Code? | 38            320 |
| | Advanced SEND (Medical Miranda) |

Enter the Chief Complaint code that most closely describes the foremost symptom or incident (1st party) If breathing appears to be INEFFECTIVE, back up to change the Breathing auto-answer from "Yes."

Critical Caller Danger Instructions pdc
MPDS 13.1.105 10/26/2017 | O: NAE
C: NAE | 45-Year-Old, Male, Conscious, Not Breathing.

Paramount for Medical

File  View  Spec Logs  Options  Go to Language  Tabs  Version  About ProQA

4:00  38: Advanced SEND (Medical Miranda)

| Entry | KQ | PDI/CEI | DLS | Summary |

1. Ø Select the problem category.

Injuries (TRAUMA)
Bleeding (TRAUMA)
MEDICAL
Bleeding (non-traumatic)
Traffic/Transportation incident
EXCITED DELIRIUM
Tasered
Unknown

323

| Question Answers | Additional Information | Probl Suffix |

321

POSSIBLY DANGEROUS Body Area
- Abdomen
- Amputation (excluding finger/toe)
- Back
- Chest (breathing normally)
- Genitalia
- Groin
- Head (alert)
- Hip/Pelvis
- Leg, upper
- Neck (breathing normally)

NOT DANGEROUS Body Area
- Ankle
- Arm, upper
- Collar bone (clavicle)
- Elbow
- Foot
- Forearm
- Hand
- Knee
- Leg, lower
- Shoulder
- Tailbone (coccyx)
- Toe
- Wrist

INEFFECTIVE BREATHING
The following, or reasonable equivalents, when volunteered at any point during case Entry (code as ECHO on 2,6,9,11,15,31):
- "Barely breathing"
- "Can't breathe at all"
- "Fighting for air"
- "Gasping for air" (AGONAL BREATHING)
- "Just a little" (AGONAL BREATHING)
- "Making funny noises" (AGONAL BREATHING)

| pdc MPDS 13.1.105 10/26/2017 | O: NAE C: NAE | 45-Year-Old, Male, Conscious, Not Breathing. |

```
Paramount for Medical
File  View  Spec Logs  Options  Go to Language  Tabs  Version  About ProQA
```

19:37   38: Advanced SEND (Medical Miranda)

| Entry | KQ | PDI/CEI | DLS | Summary |

2. Ø Type of injuries/incident:

325

| Question Answers | Additional Information | Probl Suffi |

NOT DANGEROUS body area
POSSIBLY DANGEROUS body area
Chest
Neck
Head
Fall (ground level)
MINOR hemorrhage
Minor injuries
Critical injuries 1. The problem category is injuries (TRAUMA).

322 pdc
MPDS 13.1.105 10/26/2017

O: NAE
C: NAE

45-Year-Old, Male, Conscious, Not Breathing.

Paramount for Medical

File View Spec Logs Options Go to Language Tabs Version About ProQA

22:15 | 38: Advanced SEND (Medical Miranda)

| Entry | KQ | PDI/CEI | DLS | Summary |

3. Is he completely alert (responding appropriately)?

Yes
No
Unknown

| Question Answers | Additional Information | Problem Suffixes | Determinants w/ Suffixes | Det. Codes |

1. The problem category is injuries (TRAUMA).
2. An officer reports an injury to a POSSIBLY DANGEROUS body area.

322 pdc
MPDS 13.1.105 10/26/2017

O: NAE
C: NAE

45-Year-Old, Male, Conscious, Not Breathing.

```
Paramount for Medical                                              [X]
File  View  Spec Logs  Options  Go to Language  Tabs  Version  About ProQA
[icons row]
  24:07    [ 38: Advanced SEND (Medical Miranda)           ]

Entry    |    KQ    |   PDI/CEI   |    DLS    |  Summary
                       [←]            [→]

4. Is he having any difficulty breathing?     | No      |
(Ø Only ask if "difficult breathing" status was | Yes    |
not provided in Case Entry.)                   | Unknown |

Question  | Additional  |  Problem  | Determinants | Det. Codes
 Answers   | Information |  Suffixes |  w/ Suffixes |

1. The problem category is injuries (TRAUMA).
2. An officer reports an injury to a POSSIBLY DANGEROUS body area.
3. An officer reports he is completely alert (responding appropriately).

322 pdc                       | O: NAE |
MPDS 13.1.105 10/26/2017  | C: NAE | 45-Year-Old, Male, Conscious, Not Breathing.
```

```
Paramount for Medical                                          [X]
 File  View  Spec Logs  Options  Go to Language  Tabs  Version  About ProQA
 [+][X][☎][●][≡][◉][⇅][👤][⊗][☢][☣][Ⓥ][☠][❓][👥][↓][🚶][☹][○][👤]

24:41   [ 38: Advanced SEND (Medical Miranda)            ]   [☀]

Entry      KQ        PDI/CEI        DLS         Summary
                   [ ← ]              [ → ]

5. Is there any SERIOUS bleeding (spurting or  | No bleeding now
  pouring)?                                      | Yes, SERIOUS
                                                 | Unknown
                                                 | Bleeding, not serious Question    Additional    Problem    Determinants
  Answers     Information   Suffixes   w/ Suffixes      Det. Codes 1. The problem category is injuries (TRAUMA).
  2. An officer reports an injury to a POSSIBLY DANGEROUS body area.
  3. An officer reports he is completely alert (responding appropriately).
  4. He is having difficulty breathing.

322 pdc                      O: NAE
  MPDS 13.1.105 10/26/2017 C: NAE  45-Year-Old, Male, Conscious, Not Breathing.
```

```
Paramount for Medical
File  View  Spec Logs  Options  Go to Language  Tabs  Version  About ProQA
```

25:13  38: Advanced SEND (Medical Miranda)

| Entry | KQ | PDI/CEI | DLS | Summary |

6. ∅ Officer request of a specific response mode?

- No
- HOT (lights-and-siren)
- COLD (routine)

| Question Answers | Additional Information | Problem Suffixes | Determinants w/ Suffixes | Det. Codes |

1. The problem category is injuries (TRAUMA).
2. An officer reports an injury to a POSSIBLY DANGEROUS body area.
3. An officer reports he is completely alert (responding appropriately).
4. He is having difficulty breathing.
5. There is no bleeding now.

322 pdc
MPDS 13.1.105 10/26/2017

O: NAE
C: NAE

45-Year-Old, Male, Conscious, Not Breathing.

FIG. 3G 300   326

```
Paramount for Medical                                              [X]
File  View  Spec Logs  Options  Go to Language  Tabs  Version  About ProQA
[icons]
27:05       38: Advanced SEND (Medical Miranda)
   Entry          KQ         PDI/CEI         DLS         Summary
                              ←          Send: 38-D-7 →
```

KQ Answers:
1. The problem category is injuries (TRAUMA).
2. An officer reports an injury to a POSSIBLY DANGEROUS body area.
3. An officer reports he is completely alert (responding appropriately).
4. He is having difficulty breathing.
5. There is no bleeding now.
6. A specific response mode has not been requested.

324

| Determinants | Responses (user-defined) |
|---|---|
|    3 Minor illness | |
|    4 MINOR hemorrhage | |
|    5 Chest pain/discomfort < 35 (without priority symptoms) | |
|    6 Fall (ground level) | |
| B 0 Override | |
|    1 POSSIBLY DANGEROUS body area | |
|    2 SERIOUS hemorrhage | |
|    3 Tasered | |
|    4 Unknown status (TRAUMA) | |
| C 0 Override | |
|    1 Chest pain/discomfort ≥ 35     328 | |
|    2 Childbirth | |
|    3 Seizure | |
|    4 STROKE | |
|    5 Serious illness | |
|    6 Unknown status (MEDICAL) | |
| D 0 Override | |
|    1 Reported EXCITED DELIRIUM | |
|    2 HIGH VELOCITY impact | |
|    3 Critical injuries | |
|    4 Multiple victims | |
|    5 Unconscious | |
|    6 Not alert | |
|    7 Difficulty breathing | Delta | pdc
MPDS 13.1.105 10/26/2017 | O: NAE
C: NAE | 45-Year-Old, Male, Conscious, Not Breathing.

```
Paramount for Medical                                              [X]
File  View  Spec Logs  Options  Go to Language  Tabs  Version  About ProQA
[icons row]
  24:41    [38: Advanced SEND (Medical Miranda)]           [sunburst]

┌─Entry──┐┌──KQ──┐┌─PDI/CEI─┐┌──DLS──┐┌─Summary─┐
           ┌──←──┐  ┌──→──┐

1. Ø Select the problem category.     ┌─────────────────────────────┐
                                      │ Injuries (TRAUMA)           │
                                      │ [Bleeding (TRAUMA)]         │
                                      │ MEDICAL                     │
  ┌Question ┐┌Additional ┐┌Probl│ Bleeding (non-traumatic)    │
  │Answers  ││Information││Suffi│ Traffic/Transportation incident
                                      │ EXCITED DELIRIUM            │
                                      │ Tasered                     │
                                      │ Unknown                     │
                                      └─────────────────────────────┘
POSSIBLY DANGEROUS Body Area
  ● Abdomen                              ● Groin
  ● Amputation (excluding finger/toe)    ● Head (alert)
  ● Back                                 ● Hip/Pelvis
  ● Chest (breathing normally)           ● Leg, upper
  ● Genitalia                            ● Neck (breathing normally)

NOT DANGEROUS Body Area
  ● Ankle                                ● Hand
  ● Arm, upper                           ● Knee
  ● Collar bone (clavicle)               ● Leg, lower
  ● Elbow                                ● Shoulder
  ● Foot                                 ● Tailbone (coccyx)
  ● Forearm                              ● Toe
                                         ● Wrist INEFFECTIVE BREATHING
    The following, or reasonable equivalents, when volunteered at any point during case
    Entry (code as ECHO on 2,6,9,11,15,31):
    ● "Barely breathing"
    ● "Can't breathe at all"
    ● "Fighting for air"
    ● "Gasping for air" (AGONAL BREATHING)
    ● "Just a little" (AGONAL BREATHING)
    ● "Making funny noises" (AGONAL BREATHING)

┌─────────────────┬──────────┬─────────────────────────────────────────┐
│ pdc             │ O: NAE   │ 45-Year-Old, Male, Conscious, Breathing.│
│ MPDS 13.1.105 10/26/2017 │ C: NAE │                                  │
└─────────────────┴──────────┴─────────────────────────────────────────┘
```

Paramount for Medical

File  View  Spec Logs  Options  Go to Language  Tabs  Version  About ProQA

3:08  | 38: Advanced SEND (Medical Miranda) |

| Entry | KQ | PDI/CEI | DLS | Summary |

2. Is he completely alert (responding appropriately)?

Yes
No
Unknown

| Question Answers | Additional Information | Problem Suffixes | Determinants w/ Suffixes | Det. Codes |

1. The problem category is injuries (TRAUMA).

402 pdc
MPDS 13.1.105 10/26/2017

O: NAE
C: NAE

45-Year-Old, Male, Conscious, Breathing.

```
Paramount for Medical
File  View  Spec Logs  Options  Go to Language  Tabs  Version  About ProQA
```

4:02    38: Advanced SEND (Medical Miranda)

| Entry | KQ | PDI/CEI | DLS | Summary |

3. Is he having any difficulty breathing? (Ø Only ask if "difficulty breathing" status was not provided in Case Entry.)

No
Yes
Unknown

| Question Answers | Additional Information | Problem Suffixes | Determinants w/ Suffixes | Det. Codes |

1. The problem category is injuries (TRAUMA).
2. An officer reports he is completely alert (responding appropriately).

402 pdc
MPDS 13.1.105 10/26/2017

O: NAE
C: NAE

45-Year-Old, Male, Conscious, Breathing.

400

```
Paramount for Medical                                              ☒
File  View  Spec Logs  Options  Go to Language  Tabs  Version  About ProQA
```

4:02   38: Advanced SEND (Medical Miranda)

| Entry | KQ | PDI/CEI | DLS | Summary |

4. Is the blood spurting or pouring out?

No
Yes
Unknown
Insignificant

| Question Answers | Additional Information | Problem Suffixes | Determinants w/ Suffixes | Det. Codes |

1. The problem category is injuries (TRAUMA).
2. An officer reports he is completely alert (responding appropriately).
3. He is not having difficulty breathing.

402 pdc
MPDS 13.1.105 10/26/2017

O: NAE
C: NAE

45-Year-Old, Male, Conscious, Breathing.

```
Paramount for Medical
File  View  Spec Logs  Options  Go to Language  Tabs  Version  About ProQA
```

4:02  38: Advanced SEND (Medical Miranda)

| Entry | KQ | PDI/CEI | DLS | Summary |

5. Ø Officer request of a specific response mode?

No
HOT (lights-and-siren)
COLD (routine)

| Question Answers | Additional Information | Problem Suffixes | Determinants w/ Suffixes | Det. Codes |

1. The problem category is injuries (TRAUMA).
2. An officer reports he is completely alert (responding appropriately).
3. He is not having difficulty breathing.
4. There is blood spurting or pouring out (after dispatch, go to Control Bleeding in DLS Links).

402 pdc
MPDS 13.1.105 10/26/2017

O: NAE
C: NAE

45-Year-Old, Male, Conscious, Breathing.

FIG. 4E 400    406

```
Paramount for Medical                                                    X
File  View  Spec Logs  Options  Go to Language  Tabs  Version  About ProQA
[icons]
6:51      38: Advanced SEND (Medical Miranda)
   Entry        KQ        PDI/CEI        DLS        Summary
                     ←              Send: 38-B-2H →
```

| KQ Answers | 1. The problem category is bleeding (TRAUMA).<br>2. An officer reports he is completely alert (responding appropriately).    404<br>3. He is not having difficulty breathing.<br>4. There is blood spurting or pouring out (after dispatch, go to Control Bleeding in DLS Links).<br>5. A lights-and-siren (HOT) response has been requested. |
|---|---|

| Determinants | | Responses (user-defined) |
|---|---|---|
| A | 1 NOT DANGEROUS body area | H: |
|   | 2 Minor injuries                    408 | H: |
|   | 3 Minor illness | H: |
|   | 4 MINOR hemorrhage | H: |
|   | 5 Chest pain/discomfort < 35 (without priority symptoms) | H: |
|   | 6 Fall (ground level) | H: |
| B | 0 Override | H: |
|   | 1 POSSIBLY DANGEROUS body area | H: |
|   | 2 SERIOUS hemorrhage | H: Bravo |
|   | 3 Tasered | H: |
|   | 4 Unknown status (TRAUMA) | H: |
| C | 0 Override | H: Charlie |
|   | 1 Chest pain/discomfort ≥ 35 | H: |
|   | 2 Childbirth | H: |
|   | 3 Seizure | H: |
|   | 4 STROKE | H: |
|   | 5 Serious illness | H: |
|   | 6 Unknown status (MEDICAL) | H: |
| D | 0 Override | H: Delta |
|   | 1 Reported EXCITED DELIRIUM | H: |
|   | 2 HIGH VELOCITY impact | H: |
|   | 3 Critical injuries | H: |
|   | 4 Multiple victims | H: |

| pdc<br>MPDS 13.1.105 10/26/2017 | O: NAE<br>C: NAE | 45-Year-Old, Male, Conscious, Breathing. |
|---|---|---|

FIG. 4F

Paramount for Medical

File  View  Spec Logs  Options  Go to Language  Tabs  Version  About ProQA

24:41 | 38: Advanced SEND (Medical Miranda)

| Entry | KQ | PDI/CEI | DLS | Summary |

1. Ø Select the problem category.

- Injuries (TRAUMA)
- Bleeding (TRAUMA)
- MEDICAL
- Bleeding (non-traumatic)
- Traffic/Transportation incident
- EXCITED DELIRIUM
- Tasered
- Unknown

| Question Answers | Additional Information | Problem Suffix |

POSSIBLY DANGEROUS Body Area
- Abdomen
- Amputation (excluding finger/toe)
- Back
- Chest (breathing normally)
- Genitalia
- Groin
- Head (alert)
- Hip/Pelvis
- Leg, upper
- Neck (breathing normally)

NOT DANGEROUS Body Area
- Ankle
- Arm, upper
- Collar bone (clavicle)
- Elbow
- Foot
- Forearm
- Hand
- Knee
- Leg, lower
- Shoulder
- Tailbone (coccyx)
- Toe
- Wrist

INEFFECTIVE BREATHING
The following, or reasonable equivalents, when volunteered at any point during case Entry (code as ECHO on 2,6,9,11,15,31):
- "Barely breathing"
- "Can't breathe at all"
- "Fighting for air"
- "Gasping for air" (AGONAL BREATHING)
- "Just a little" (AGONAL BREATHING)
- "Making funny noises" (AGONAL BREATHING)

| pdc MPDS 13.1.105 10/26/2017 | O: NAE C: NAE | 45-Year-Old, Male, Conscious, Breathing. |

```
Paramount for Medical
File  View  Spec Logs  Options  Go to Language  Tabs  Version  About ProQA
```

1:04   38: Advanced SEND (Medical Miranda)

| Entry | KQ | PDI/CEI | DLS | Summary |

1. Ø Type of incident?

Chest pain/discomfort
STROKE
Seizure
Other serious illness
Minor illness

| Question Answers | Additional Information | Problem Suffixes | w/ Suffixes |

1. The problem category is MEDICAL.

pdc
MPDS 13.1.105 10/26/2017

O: NAE
C: NAE

45-Year-Old, Male, Conscious, Breathing.

Paramount for Medical

File  View  Spec Logs  Options  Go to Language  Tabs  Version  About ProQA

4:02 | 38: Advanced SEND (Medical Miranda)

| Entry | KQ | PDI/CEI | DLS | Summary |

4. Is he having any difficulty breathing? (Ø Only ask if "difficulty breathing" status was not provided in Case Entry.)

No
Yes
Unknown

| Question Answers | Additional Information | Problem Suffixes | Determinants w/ Suffixes | Det. Codes |

1. The problem category is MEDICAL.
2. An officer reports other serious illness.

502 pdc
MPDS 13.1.105 10/26/2017

O: NAE
C: NAE

45-Year-Old, Male, Conscious, Breathing.

```
Paramount for Medical
File  View  Spec Logs  Options  Go to Language  Tabs  Version  About ProQA
```

4:02    38: Advanced SEND (Medical Miranda)

| Entry | KQ | PDI/CEI | DLS | Summary |

4. Ø Officer request of a specific response mode?

- No
- HOT (lights-and-siren)
- COLD (routine)

| Question Answers | Additional Information | Problem Suffixes | Determinants w/ Suffixes | Det. Codes |

1. The problem category is MEDICAL.
2. An officer reports other serious illness.
3. He is having difficulty breathing.

pdc
MPDS 13.1.105 10/26/2017

O: NAE
C: NAE

45-Year-Old, Male, Conscious, Breathing.

FIG. 5D 500     506

```
Paramount for Medical
File  View  Spec Logs  Options  Go to Language  Tabs  Version  About ProQA
3:48     38: Advanced SEND (Medical Miranda)
   Entry        KQ        PDI/CEI        DLS        Summary
                       ←           Send: 38-D-7 →
```

KQ Answers:
1. The problem category is MEDICAL.                            504
2. An officer reports other serious illness.
3. He is having difficulty breathing.
4. A specific response mode has not been requested.

| Determinants | Responses (user-defined) |
|---|---|
| 3 MINOR illness | |
| 4 MINOR hemorrhage | |
| 5 Chest pain/discomfort < 35 (without priority symptoms) | |
| 6 Fall (ground level) | |
| B 0 Override | |
| 1 POSSIBLY DANGEROUS body area | |
| 2 SERIOUS hemorrhage | |
| 3 Tasered | |
| 4 Unknown status (TRAUMA) | |
| C 0 Override | |
| 1 Chest pain/discomfort ≥ 35 | |
| 2 Childbirth | |
| 3 Seizure | |
| 4 STROKE | |
| 5 Serious illness | |
| 6 Unknown status (MEDICAL) | |
| D 0 Override | |
| 1 Reported EXCITED DELIRIUM | |
| 2 HIGH VELOCITY impact | |
| 3 Critical injuries | |
| 4 Multiple victims | |
| 5 Unconscious | |
| 6 Not alert | |
| 7 Difficulty breathing | Delta |

| pdc<br>MPDS 13.1.105 10/26/2017 | O: NAE<br>C: NAE | 45-Year-Old, Male, Conscious, Breathing. |

```
Paramount for Medical                                                    [X]
 File  View  Spec Logs  Options  Go to Language  Tabs  Version  About ProQA
 [icons toolbar]
 :55    [ 38: Advanced SEND (Medical Miranda)            ]      [sunburst]

Entry         KQ         PDI/CEI         DLS         Summary
                           [←]             [→]

1. Ø Select the problem category.      Injuries (TRAUMA)
                                        Bleeding (TRAUMA)
                                        MEDICAL
                                        [Bleeding (non-traumatic)]
   Question      Additional     Probl   Traffic/Transportation incident
   Answers       Information    Suffi   EXCITED DELIRIUM
                                        Tasered
                                        Unknown POSSIBLY DANGEROUS Body Area
   ● Abdomen                            ● Groin
   ● Amputation (excluding finger/toe)  ● Head (alert)
   ● Back                               ● Hip/Pelvis
   ● Chest (breathing normally)         ● Leg, upper
   ● Genitalia                          ● Neck (breathing normally)

NOT DANGEROUS Body Area
   ● Ankle                              ● Hand
   ● Arm, upper                         ● Knee
   ● Collar bone (clavicle)             ● Leg, lower
   ● Elbow                              ● Shoulder
   ● Foot                               ● Tailbone (coccyx)
   ● Forearm                            ● Toe
                                        ● Wrist
 INEFFECTIVE BREATHING
   The following, or reasonable equivalents, when volunteered at any point during case
   Entry (code as ECHO on 2,6,9,11,15,31):
   ● "Barely breathing"
   ● "Can't breathe at all"
   ● "Fighting for air"
   ● "Gasping for air" (AGONAL BREATHING)
   ● "Just a little" (AGONAL BREATHING)
   ● "Making funny noises" (AGONAL BREATHING)

pdc                        O: NAE   45-Year-Old, Male, Conscious, Breathing.
 MPDS 13.1.105 10/26/2017   C: NAE
```

```
Paramount for Medical
File  View  Spec Logs  Options  Go to Language  Tabs  Version  About ProQA
```

4:02   38: Advanced SEND (Medical Miranda)

| Entry | KQ | PDI/CEI | DLS | Summary |

2. Is he completely alert (responding appropriately)?

Yes
No
Unknown

| Question Answers | Additional Information | Problem Suffixes | Determinants w/ Suffixes | Det. Codes |

1. The problem category is bleeding (non-traumatic).

pdc
MPDS 13.1.105 10/26/2017

O: NAE
C: NAE

45-Year-Old, Male, Conscious, Breathing.

```
Paramount for Medical
File  View  Spec Logs  Options  Go to Language  Tabs  Version  About ProQA
```

2:59   38: Advanced SEND (Medical Miranda)

| Entry | KQ | PDI/CEI | DLS | Summary |

3. Is he having any difficulty breathing? (Ø Only ask if "difficulty breathing" status was not provided in Case Entry.)

No
Yes
Unknown

| Question Answers | Additional Information | Problem Suffixes | Determinants w/ Suffixes | Det. Codes |

1. The problem category is bleeding (non-traumatic).
2. An officer reports he is not completely alert (not responding appropriately).

pdc
MPDS 13.1.105 10/26/2017
O: NAE
C: NAE
45-Year-Old, Male, Conscious, Breathing.

```
Paramount for Medical
File  View  Spec Logs  Options  Go to Language  Tabs  Version  About ProQA
```

3:38    38: Advanced SEND (Medical Miranda)

| Entry | KQ | PDI/CEI | DLS | Summary |

4. Is the bleeding SERIOUS?

No
Yes
Unknown

| Question Answers | Additional Information | Problem Suffixes | Determinants w/ Suffixes | Det. Codes |

1. The problem category is bleeding (non-traumatic).
2. An officer reports he is not completely alert (not responding appropriately).
3. He is not having difficulty breathing.

pdc
MPDS 13.1.105 10/26/2017

O: NAE
C: NAE

45-Year-Old, Male, Conscious, Breathing.

```
Paramount for Medical
File  View  Spec Logs  Options  Go to Language  Tabs  Version  About ProQA 4:12   38: Advanced SEND (Medical Miranda)

Entry    |    KQ    |   PDI/CEI   |    DLS    |   Summary

5. Ø Officer request of a specific response     No
   mode?                                        HOT (lights-and-siren)
                                                COLD (routine)

Question  | Additional  | Problem  | Determinants |
 Answers   | Information | Suffixes | w/ Suffixes  | Det. Codes 1. The problem category is bleeding (non-traumatic).
2. An officer reports he is not completely alert (not responding appropriately).
3. He is not having difficulty breathing.
4. There is no SERIOUS bleeding.

pdc                         O: NAE
 MPDS 13.1.105 10/26/2017    C: NAE   45-Year-Old, Male, Conscious, Breathing.
```

FIG. 6E 600    604

```
Paramount for Medical                                              [X]
File  View  Spec Logs  Options  Go to Language  Tabs  Version  About ProQA
[icons row]
1:14       38: Advanced SEND (Medical Miranda)
```

| Entry | KQ | PDI/CEI | DLS | Summary |

⬅            Send: 38-D-6 ➡

KQ Answers:
1. The problem category is bleeding (non-traumatic).
2. An officer reports he is not completely alert (not responding appropriately).
3. He is not having difficulty breathing.                          602
4. There is no SERIOUS bleeding.
5. A specific response mode has not been requested.

| Determinants | Responses (user-defined) |
|---|---|
|    3 MINOR illness | |
|    4 MINOR hemorrhage | |
|    5 Chest pain/discomfort < 35 (without priority symptoms) | |
|    6 Fall (ground level) | |
| B  0 Override | |
|    1 POSSIBLY DANGEROUS body area | |
|    2 SERIOUS hemorrhage | |
|    3 Tasered | |
|    4 Unknown status (TRAUMA) | |
| C  0 Override | |
|    1 Chest pain/discomfort ≥ 35 | |
|    2 Childbirth | |
|    3 Seizure | |
|    4 STROKE | |
|    5 Serious illness | |
|    6 Unknown status (MEDICAL) | |
| D  0 Override | |
|    1 Reported EXCITED DELIRIUM | |
|    2 HIGH VELOCITY impact | |
|    3 Critical injuries | |
|    4 Multiple victims | |
|    5 Unconscious | |
|    6 Not alert | Delta |

| pdc | O: NAE | 45-Year-Old, Male, Conscious, Breathing. |
| MPDS 13.1.105 10/26/2017 | C: NAE | |

```
Paramount for Medical                                                    [X]
 File  View  Spec Logs  Options  Go to Language  Tabs  Version  About ProQA
 [icons toolbar]
 :56    [ 38: Advanced SEND (Medical Miranda) ]
```

| Entry | KQ | PDI/CEI | DLS | Summary |

1. Ø Select the problem category.      Injuries (TRAUMA)
                                       Bleeding (TRAUMA)
                                       MEDICAL
                                       Bleeding (non-traumatic)
| Question | Additional   | Probl | Traffic/Transportation incident
| Answers  | Information  | Suffi | EXCITED DELIRIUM
                                       Tasered
                                       Unknown POSSIBLY DANGEROUS Body Area
- Abdomen
- Amputation (excluding finger/toe)
- Back
- Chest (breathing normally)
- Genitalia

- Groin
- Head (alert)
- Hip/Pelvis
- Leg, upper
- Neck (breathing normally)

NOT DANGEROUS Body Area
- Ankle
- Arm, upper
- Collar bone (clavicle)
- Elbow
- Foot
- Forearm

- Hand
- Knee
- Leg, lower
- Shoulder
- Tailbone (coccyx)
- Toe
- Wrist

INEFFECTIVE BREATHING
  The following, or reasonable equivalents, when volunteered at any point during case Entry (code as ECHO on 2,6,9,11,15,31):
- "Barely breathing"
- "Can't breathe at all"
- "Fighting for air"
- "Gasping for air" (AGONAL BREATHING)
- "Just a little" (AGONAL BREATHING)
- "Making funny noises" (AGONAL BREATHING)

| pdc                            | O: NAE | 45-Year-Old, Male, Conscious, Breathing. |
| MPDS 13.1.105 10/26/2017       | C: NAE |                                          |

```
Paramount for Medical
File  View  Spec Logs  Options  Go to Language  Tabs  Version  About ProQA
```

2:06   38: Advanced SEND (Medical Miranda)

| Entry | KQ | PDI/CEI | DLS | Summary |

3. Is he completely alert (responding appropriately)?

Yes
No
Unknown

| Question Answers | Additional Information | Problem Suffixes | Determinants w/ Suffixes | Det. Codes |

1. The problem category is a traffic/transportation incident.
2. An officer reports there are critical injuries.

pdc
MPDS 13.1.105 10/26/2017

O: NAE
C: NAE

45-Year-Old, Male, Conscious, Breathing.

```
Paramount for Medical
File  View  Spec Logs  Options  Go to Language  Tabs  Version  About ProQA
```

2:49   38: Advanced SEND (Medical Miranda)

| Entry | KQ | PDI/CEI | DLS | Summary |

4. Is he having any difficulty breathing? (Ø Only ask if "difficulty breathing" status was not provided in Case Entry.)

No
Yes
Unknown

| Question Answers | Additional Information | Problem Suffixes | Determinants w/ Suffixes | Det. Codes |

1. The problem category is a traffic/transportation incident.
2. An officer reports there are critical injuries.
3. An officer reports he is completely alert (responding appropriately).

pdc
MPDS 13.1.105 10/26/2017

O: NAE
C: NAE

45-Year-Old, Male, Conscious, Breathing.

Paramount for Medical

File  View  Spec Logs  Options  Go to Language  Tabs  Version  About ProQA

3:38  38: Advanced SEND (Medical Miranda)

| Entry | KQ | PDI/CEI | DLS | Summary |

5. Is there any SERIOUS bleeding (spurting or pouring)?

No bleeding now
Yes, SERIOUS
Unknown
Bleeding, not serious

| Question Answers | Additional Information | Problem Suffixes | Determinants w/ Suffixes | Det. Codes |

1. The problem category is a traffic/transportation incident.
2. An officer reports there are critical injuries.
3. An officer reports he is completely alert (responding appropriately).
4. It's not known if he has difficulty breathing.

pdc
MPDS 13.1.105 10/26/2017

O: NAE
C: NAE

45-Year-Old, Male, Conscious, Breathing.

```
Paramount for Medical
File  View  Spec Logs  Options  Go to Language  Tabs  Version  About ProQA
```

4:21    38: Advanced SEND (Medical Miranda)

| Entry | KQ | PDI/CEI | DLS | Summary |

6. Ø Officer request of a specific response mode?

No
    HOT (lights-and-siren)
    COLD (routine)

| Question Answers | Additional Information | Problem Suffixes | Determinants w/ Suffixes | Det. Codes |

1. The problem category is a traffic/transportation incident.
2. An officer reports there are critical injuries.
3. An officer reports he is completely alert (responding appropriately).
4. It's not known if he has difficulty breathing.
5. There is some bleeding, not serious.

pdc
MPDS 13.1.105 10/26/2017

O: NAE
C: NAE

45-Year-Old, Male, Conscious, Breathing.

FIG. 7F 700    704

```
Paramount for Medical                                              [X]
File  View  Spec Logs  Options  Go to Language  Tabs  Version  About ProQA
[icons toolbar]
5:06        38: Advanced SEND (Medical Miranda)
```

| Entry | KQ | PDI/CEI | DLS | Summary |

Send: 38-D-3H →

KQ Answers:
1. The problem category is a traffic/transportation incident.
2. An officer reports there are critical injuries.
3. An officer reports he is not completely alert (responding appropriately).           702
4. It's not known if he has difficulty breathing.
5. There is some bleeding, not serious.
6. A lights-and-siren (HOT) response has been requested.

| Determinants | Responses (user-defined) |
|---|---|
| A 1 NOT DANGEROUS body area | H: |
| 2 Minor injuries | H: |
| 3 Minor illness | H: |
| 4 MINOR hemorrhage | H: |
| 5 Chest pain/discomfort < 35 (without priority symptoms) | H: |
| 6 Fall (ground level) | H: |
| B 0 Override | H: |
| 1 POSSIBLY DANGEROUS body area | H: |
| 2 SERIOUS hemorrhage | H: |
| 3 Tasered | H: |
| 4 Unknown status (TRAUMA) | H: |
| C 0 Override | H: |
| 1 Chest pain/discomfort ≥ 35 | H: |
| 2 Childbirth | H: |
| 3 Seizure | H: |
| 4 STROKE | H: |
| 5 Serious illness | H: |
| 6 Unknown status (MEDICAL) | H: |
| D 0 Override | H: |
| 1 Reported EXCITED DELIRIUM | H: |
| 2 HIGH VELOCITY impact | H: |
| 3 Critical injuries | H: Delta |

| pdc<br>MPDS 13.1.105 10/26/2017 | O: NAE<br>C: NAE | 45-Year-Old, Male, Conscious, Breathing. |

Paramount for Medical

File  View  Spec Logs  Options  Go to Language  Tabs  Version  About ProQA

1:54  |  38: Advanced SEND (Medical Miranda)  |

| Entry | KQ | PDI/CEI | DLS | Summary |

1. Ø Select the problem category.

- Injuries (TRAUMA)
- Bleeding (TRAUMA)
- MEDICAL
- Bleeding (non-traumatic)
- Traffic/Transportation incident
- EXCITED DELIRIUM
- Tasered
- Unknown

| Question Answers | Additional Information | Problem Suffix |

POSSIBLY DANGEROUS Body Area
- Abdomen
- Amputation (excluding finger/toe)
- Back
- Chest (breathing normally)
- Genitalia
- Groin
- Head (alert)
- Hip/Pelvis
- Leg, upper
- Neck (breathing normally)

NOT DANGEROUS Body Area
- Ankle
- Arm, upper
- Collar bone (clavicle)
- Elbow
- Foot
- Forearm
- Hand
- Knee
- Leg, lower
- Shoulder
- Tailbone (coccyx)
- Toe
- Wrist

INEFFECTIVE BREATHING
The following, or reasonable equivalents, when volunteered at any point during case Entry (code as ECHO on 2,6,9,11,15,31):
- "Barely breathing"
- "Can't breathe at all"
- "Fighting for air"
- "Gasping for air" (AGONAL BREATHING)
- "Just a little" (AGONAL BREATHING)
- "Making funny noises" (AGONAL BREATHING)

| pdc<br>MPDS 13.1.105 10/26/2017 | O: NAE<br>C: NAE | 28-Year-Old, Female, Conscious, Breathing. |

```
Paramount for Medical                                              [X]
File  View  Spec Logs  Options  Go to Language  Tabs  Version  About ProQA
```

2:35   38: Advanced SEND (Medical Miranda)

| Entry | KQ | PDI/CEI | DLS | Summary |

3. Is she in protective custody now?

Yes
No
Unknown

| Question Answers | Additional Information | Problem Suffixes | Determinants w/ Suffixes | Det. Codes |

1. The problem category is EXCITED DELIRIUM.
2. A state of EXCITED DELIRIUM obviously infers that she is not fully alert.

802 pdc
MPDS 13.1.105 10/26/2017
O: NAE
C: NAE
28-Year-Old, Female, Conscious, Breathing.

```
Paramount for Medical
File  View  Spec Logs  Options  Go to Language  Tabs  Version  About ProQA
```

5:23   38: Advanced SEND (Medical Miranda)

| Entry | KQ | PDI/CEI | DLS | Summary |

4. Ø Officer request of a specific response mode?

- No
- HOT (lights-and-siren)
- COLD (routine)

| Question Answers | Additional Information | Problem Suffixes | Determinants w/ Suffixes | Det. Codes |

1. The problem category is EXCITED DELIRIUM.
2. A state of EXCITED DELIRIUM obviously infers that she is not fully alert.
3. She is not in protective custody.

pdc
MPDS 13.1.105 10/26/2017

O: NAE
C: NAE

28-Year-Old, Female, Conscious, Breathing.

FIG. 8C 800    806

```
Paramount for Medical                                                  [X]
File  View  Spec Logs  Options  Go to Language  Tabs  Version  About ProQA
[icons]
5:56      38: Advanced SEND (Medical Miranda)
```

| Entry | KQ | PDI/CEI | DLS | Summary |

← → Send: 38-D-1C →

KQ Answers
1. The problem category is EXCITED DELIRIUM.
2. A state of EXCITED DELIRIUM obviously infers that she is not fully alert.
3. She is not in protective custody.                                        804
4. A routine (COLD) response has been requested.

| Determinants | Responses (user-defined) |
|---|---|
| A 1 NOT DANGEROUS body area | C: |
|    2 Minor injuries | C: |
|    3 Minor illness | C: |
|    4 MINOR hemorrhage | C: |
|    5 Chest pain/discomfort < 35 (without priority symptoms) | C: |
|    6 Fall (ground level) | C: |
| B 0 Override | C: |
|    1 POSSIBLY DANGEROUS body area | C: |
|    2 SERIOUS hemorrhage | C: |
|    3 Tasered | C: |
|    4 Unknown status (TRAUMA) | C: |
| C 0 Override | C: |
|    1 Chest pain/discomfort ≥ 35 | C: |
|    2 Childbirth | C: |
|    3 Seizure | C: |
|    4 STROKE | C: |
|    5 Serious illness | C: |
|    6 Unknown status (MEDICAL) | C: |
| D 0 Override | C: |
|    1 Reported EXCITED DELIRIUM | C:  Delta |
|    2 HIGH VELOCITY impact | C: |
|    3 Critical injuries | C: |

| pdc<br>MPDS 13.1.105 10/26/2017 | O: NAE<br>C: NAE | 28-Year-Old, Female, Conscious, Breathing. |

FIG. 8D

Paramount for Medical

File  View  Spec Logs  Options  Go to Language  Tabs  Version  About ProQA

:41   38: Advanced SEND (Medical Miranda)

| Entry | KQ | PDI/CEI | DLS | Summary |

1. Ø Select the problem category.

- Injuries (TRAUMA)
- Bleeding (TRAUMA)
- MEDICAL
- Bleeding (non-traumatic)
- Traffic/Transportation incident
- EXCITED DELIRIUM
- Tasered
- Unknown

| Question Answers | Additional Information | Problem Suffix |

POSSIBLY DANGEROUS Body Area
- Abdomen
- Amputation (excluding finger/toe)
- Back
- Chest (breathing normally)
- Genitalia
- Groin
- Head (alert)
- Hip/Pelvis
- Leg, upper
- Neck (breathing normally)

NOT DANGEROUS Body Area
- Ankle
- Arm, upper
- Collar bone (clavicle)
- Elbow
- Foot
- Forearm
- Hand
- Knee
- Leg, lower
- Shoulder
- Tailbone (coccyx)
- Toe
- Wrist

INEFFECTIVE BREATHING
The following, or reasonable equivalents, when volunteered at any point during case Entry (code as ECHO on 2,6,9,11,15,31):
- "Barely breathing"
- "Can't breathe at all"
- "Fighting for air"
- "Gasping for air" (AGONAL BREATHING)
- "Just a little" (AGONAL BREATHING)
- "Making funny noises" (AGONAL BREATHING)

| pdc MPDS 13.1.105 10/26/2017 | O: NAE C: NAE | 28-Year-Old, Female, Conscious, Breathing. |

```
Paramount for Medical                                                    [X]
File  View  Spec Logs  Options  Go to Language  Tabs  Version  About ProQA
```

| | 38: Advanced SEND (Medical Miranda) | |
|---|---|---|
| 1:38 | | |

| Entry | KQ | PDI/CEI | DLS | Summary |
|---|---|---|---|---|

2. Is she completely alert (responding appropriately)?

Yes
No
Unknown

| Question Answers | Additional Information | Problem Suffixes | Determinants w/ Suffixes | Det. Codes |
|---|---|---|---|---|

1. The problem category is a tasered patient.

pdc
MPDS 13.1.105 10/26/2017

O: NAE
C: NAE

28-Year-Old, Female, Conscious, Breathing.

```
Paramount for Medical
File  View  Spec Logs  Options  Go to Language  Tabs  Version  About ProQA
```

:45   38: Advanced SEND (Medical Miranda)

| Entry | KQ | PDI/CEI | DLS | Summary |

3. Is she in protective custody now?

Yes
No
Unknown

| Question Answers | Additional Information | Problem Suffixes | Determinants w/ Suffixes | Det. Codes |

1. The problem category is a tasered patient.
2. An officer reports she is completely alert (responding appropriately).

pdc
MPDS 13.1.105 10/26/2017

O: NAE
C: NAE

28-Year-Old, Female, Conscious, Breathing.

```
Paramount for Medical                                                    [X]
File  View  Spec Logs  Options  Go to Language  Tabs  Version  About ProQA
[icons toolbar]
   1:39    [ 38: Advanced SEND (Medical Miranda)          ]

Entry    |    KQ    |   PDI/CEI   |    DLS    |   Summary
                         (←)              (→)

4. Ø Officer request of a specific response      No
   mode?                                         HOT (lights-and-siren)
                                                 COLD (routine)

Question   | Additional  | Problem   | Determinants | Det. Codes
  Answers    | Information | Suffixes  | w/ Suffixes  |

1. The problem category is a tasered patient.
2. An officer reports she is completely alert (responding appropriately).
3. She is in protective custody.

pdc                        O: NAE
  MPDS 13.1.105 10/26/2017   C: NAE    28-Year-Old, Female, Conscious, Breathing.
```

FIG. 9D

Paramount for Medical

File  View  Spec Logs  Options  Go to Language  Tabs  Version  About ProQA

2:13  38: Advanced SEND (Medical Miranda)

| Entry | KQ | PDI/CEI | DLS | Summary |

Send: 38-B-3C

KQ Answers
1. The problem category is a tasered patient.
2. An officer reports she is completely alert (responding appropriately).
3. She is in protective custody.
4. A routine (COLD) response has been requested.

902

| Determinants | Responses (user-defined) |
|---|---|
| A  1  NOT DANGEROUS body area | C: |
| 2  Minor injuries | C: |
| 3  Minor illness | C: |
| 4  MINOR hemorrhage | C: |
| 5  Chest pain/discomfort < 35 (without priority symptoms) | C: |
| 6  Fall (ground level) | C: |
| B  0  Override | C: |
| 1  POSSIBLY DANGEROUS body area | C: |
| 2  SERIOUS hemorrhage | C: |
| 3  Tasered | C:  Bravo |
| 4  Unknown status (TRAUMA) | C: |
| C  0  Override | C:  Charlie |
| 1  Chest pain/discomfort ≥ 35 | C: |
| 2  Childbirth | C: |
| 3  Seizure | C: |
| 4  STROKE | C: |
| 5  Serious illness | C: |
| 6  Unknown status (MEDICAL) | C: |
| D  0  Override | C:  Delta |
| 1  Reported EXCITED DELIRIUM | C: |
| 2  HIGH VELOCITY impact | C: |
| 3  Critical injuries | C: |

| pdc | O: NAE | 28-Year-Old, Female, Conscious, Breathing. |
| MPDS 13.1.105 10/26/2017 | C: NAE | |

```
Paramount for Medical                                              [X]
File  View  Spec Logs  Options  Go to Language  Tabs  Version  About ProQA
[icons toolbar]
:41    [ 38: Advanced SEND (Medical Miranda) ]
```

| Entry | KQ | PDI/CEI | DLS | Summary |

1. Ø Select the problem category.

Dropdown:
- Injuries (TRAUMA)
- Bleeding (TRAUMA)
- MEDICAL
- Bleeding (non-traumatic)
- Traffic/Transportation incident
- EXCITED DELIRIUM
- Tasered
- Unknown

| Question Answers | Additional Information | Problem Suffix |

POSSIBLY DANGEROUS Body Area
- Abdomen
- Amputation (excluding finger/toe)
- Back
- Chest (breathing normally)
- Genitalia
- Groin
- Head (alert)
- Hip/Pelvis
- Leg, upper
- Neck (breathing normally)

NOT DANGEROUS Body Area
- Ankle
- Arm, upper
- Collar bone (clavicle)
- Elbow
- Foot
- Forearm
- Hand
- Knee
- Leg, lower
- Shoulder
- Tailbone (coccyx)
- Toe
- Wrist

INEFFECTIVE BREATHING
  The following, or reasonable equivalents, when volunteered at any point during case Entry (code as ECHO on 2,6,9,11,15,31):
- "Barely breathing"
- "Can't breathe at all"
- "Fighting for air"
- "Gasping for air" (AGONAL BREATHING)
- "Just a little" (AGONAL BREATHING)
- "Making funny noises" (AGONAL BREATHING)

| pdc<br>MPDS 13.1.105 10/26/2017 | O: NAE<br>C: NAE | 28-Year-Old, Female, Conscious, Breathing. |

```
Paramount for Medical                                              [X]
File  View  Spec Logs  Options  Go to Language  Tabs  Version  About ProQA
```

| Entry | KQ | PDI/CEI | DLS | Summary |

2:15   38: Advanced SEND (Medical Miranda)

3. Is she completely alert (responding appropriately)?

Yes
No
Unknown

| Question Answers | Additional Information | Problem Suffixes | Determinants w/ Suffixes | Det. Codes |

1. The problem category is unknown.
2. This is a MEDICAL situation.

1002 pdc
MPDS 13.1.105 10/26/2017

O: NAE
C: NAE

28-Year-Old, Female, Conscious, Breathing.

Paramount for Medical

File  View  Spec Logs  Options  Go to Language  Tabs  Version  About ProQA

3:06  | 38: Advanced SEND (Medical Miranda) |

| Entry | KQ | PDI/CEI | DLS | Summary |

4. Is she having any difficulty breathing? (Ø Only ask if "difficulty breathing" status was not provided in Case Entry.)

| No |
| Yes |
| Unknown |

| Question Answers | Additional Information | Problem Suffixes | Determinants w/ Suffixes | Det. Codes |

1. The problem category is unknown.
2. This is a MEDICAL situation.
3. An officer reports she is not completely alert (not responding appropriately).

pdc
MPDS 13.1.105 10/26/2017

O: NAE
C: NAE

28-Year-Old, Female, Conscious, Breathing.

```
Paramount for Medical
File  View  Spec Logs  Options  Go to Language  Tabs  Version  About ProQA
```

3:47  38: Advanced SEND (Medical Miranda)

| Entry | KQ | PDI/CEI | DLS | Summary |

5. Ø Officer request of a specific response mode?

No
HOT (lights-and-siren)
COLD (routine)

| Question Answers | Additional Information | Problem Suffixes | Determinants w/ Suffixes | Det. Codes |

1. The problem category is unknown.
2. This is a MEDICAL situation.
3. An officer reports she is not completely alert (not responding appropriately).
4. She is not having difficulty breathing.

pdc
MPDS 13.1.105 10/26/2017
O: NAE
C: NAE
28-Year-Old, Female, Conscious, Breathing.

FIG. 10E

Paramount for Medical

File  View  Spec Logs  Options  Go to Language  Tabs  Version  About ProQA

4:13  38: Advanced SEND (Medical Miranda)

| Entry | KQ | PDI/CEI | DLS | Summary |

Send: 38-D-6H

KQ Answers:
1. The problem category is unknown.
2. This is a MEDICAL situation.
3. An officer reports she is not completely alert (not responding appropriately).
4. She is not having difficulty breathing.
5. A lights-and-siren (HOT) response has been requested.

| Determinants | Responses (user-defined) |
|---|---|
| 3 Minor illness | H: |
| 4 MINOR hemorrhage | H: |
| 5 Chest pain/discomfort < 35 (without priority symptoms) | H: |
| 6 Fall (ground level) | H: |
| B 0 Override | H: |
| 1 POSSIBLY DANGEROUS body area | H: |
| 2 SERIOUS hemorrhage | H: |
| 3 Tasered | H: |
| 4 Unknown status (TRAUMA) | H: |
| C 0 Override | H: |
| 1 Chest pain/discomfort ≥ 35 | H: |
| 2 Childbirth | H: |
| 3 Seizure | H: |
| 4 STROKE | H: |
| 5 Serious illness | H: |
| 6 Unknown status (MEDICAL) | H: |
| D 0 Override | H: |
| 1 Reported EXCITED DELIRIUM | H: |
| 2 HIGH VELOCITY impact | H: |
| 3 Critical injuries | H: |
| 4 Multiple victims | H: |
| 5 Unconscious | H: |
| 6 Not alert | H: Delta | pdc
MPDS 13.1.105 10/26/2017

O: NAE
H: NAE

Caller Statement: 28 yr. Old Female

| Always provide to dispatch on medical calls: |
|---|
| 1. Main problem or incident type? (be specific) |

| Medical: | Bleeding: | Injuries: | Traffic: | Excited Del. or Tasered: |
|---|---|---|---|---|
| Minor Illness | MINOR (ext.) | Area Inj. | Minor Inj. | In custody |
| Serious Illness (Chest Pain, Stroke, Seizure, etc.) | SERIOUS (ext.) Internal (from inside) | LONG FALL Critical | Critical Inj. High Velocity Impact | Not in custody | a. (Accident) More than one injured?

2. Approximate age?

3. Conscious: Yes / No...or not alert?

4. Breathing: Yes / No...or difficulty?

5. (Illness case):
   Is there chest pain or serious illness?

6. (Accident/injury case):
   Is there severe bleeding (spurting/ pouring)?

7. (Response mode):
   Do you need a lights-and-siren response?

FIG. 11B

Case Entry

| | | 1204 |
|---|---|---|
| Location: | 1206 | |
| Phone #: | 1208 | |
| Problem Description: | 1210 | |
| With Patient Now: | Yes 1212 | |
| Num Hurt/Sick: | 1 1214 | |
| Patient Age: | 45 1216 | |
| Gender: | Male 1218 | |
| Is he awake (conscious)? | Yes 1220 | |
| Is Patient Breathing: | No 1222 | |

1224

Next →

EXPEDITED DISPATCH PROTOCOL SYSTEM AND METHOD

CROSS-REFERENCE TO RELATED APPLICATIONS

This patent application claims priority to U.S. Patent Application No. 62/659,947 entitled EXPEDITED DISPATCH PROTOCOL SYSTEM AND METHOD COPYRIGHT NOTICE, filed Apr. 19, 2018, which is incorporated herein by reference in its entirety.

COPYRIGHT NOTICE

© 2019 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

The present disclosure relates to computer systems and methods for providing medical emergency interrogation, information collection, instruction, and dispatch. More specifically, the disclosure is directed to computer-implemented protocols to enable a dispatcher to process medical response requests in an accurate, consistent, and systematic manner by guiding the dispatcher during interrogation, information collection, response determination, and information provider instruction.

BRIEF DESCRIPTION OF THE DRAWINGS

FIGS. 3A-3H illustrate embodiments of a user interface for an emergency dispatch protocol.

FIGS. 4A-4F illustrate embodiments of a user interface for an emergency dispatch protocol.

FIGS. 5A-5E illustrate embodiments of a user interface for an emergency dispatch protocol.

FIGS. 6A-6F illustrate embodiments of a user interface for an emergency dispatch protocol.

FIGS. 7A-7G illustrate embodiments of a user interface for an emergency dispatch protocol.

FIGS. 8A-8D illustrate embodiments of a user interface for an emergency dispatch protocol.

FIGS. 9A-9E illustrate embodiments of a user interface for an emergency dispatch protocol.

FIGS. 10A-10F illustrate embodiments of a user interface for an emergency dispatch protocol.

FIGS. 11A and 11B illustrate an embodiment of a reference card for use by a first responder.

FIGS. 12A-12H illustrate embodiments of a user interface of a software application for use with an emergency dispatch protocol.

DETAILED DESCRIPTION

Figure 1:
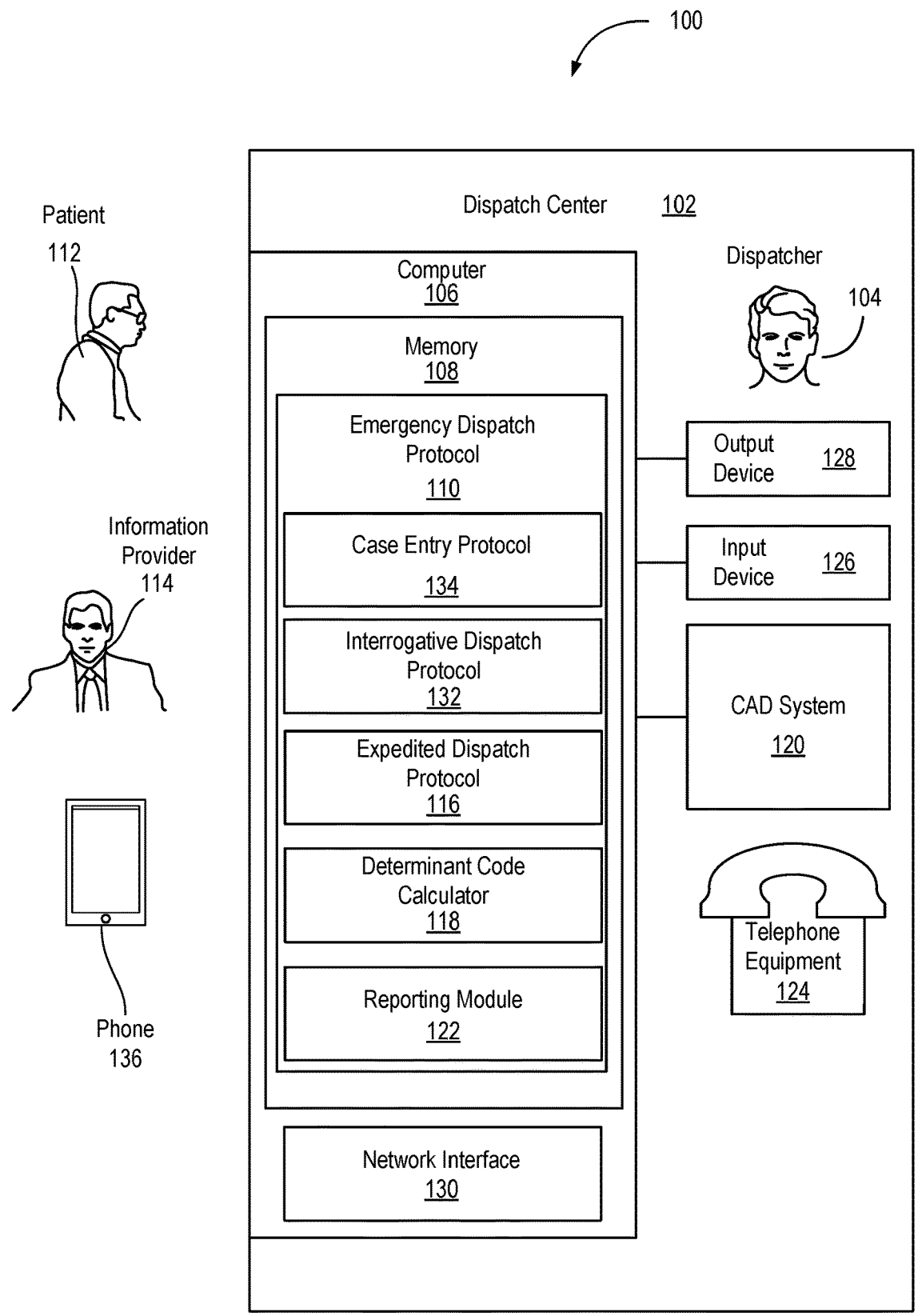
FIG. 1 is a block diagram of a dispatch protocol system and method, according to one embodiment.

Emergency medical dispatch services greatly benefit from emergency medical protocols to provide uniform and consistent results. The emergency medical protocols include a systematic method of interrogation of information providers with preprogrammed inquiries to eliminate variability due to different skills of the individual dispatchers and the need for the dispatcher to attempt to recall the appropriate inquiries and instructions each time a call is received. Emergency medical protocols allow emergency dispatchers to send the appropriate response personnel and emergency vehicles, and decide whether to use lights-and-siren responses. This allows reasonable use of resources and lights-and-siren responses to reduce the risk of collision.

It has long been the experience that emergency medical protocols improve accuracy and effectiveness of gathered information, thereby reserving responders for the most critical emergencies. A further benefit of emergency medical protocols is to reduce dispatcher burnout and stress by improving information relayed to emergency responders while simultaneously providing such responders with increased safety awareness and knowledge of the medical emergency. Medical dispatch systems with emergency medical protocols further provide programmed instructions for patient care.

Emergency dispatch systems anticipate that information providers requesting a medical response are inexperienced and will need to be guided through the inquiries. However, often a trained first responder will contact a dispatch service, and disclosed herein is an expedited protocol that saves time and energy by not prompting an information provider who is a trained first responder for each query.

A first responder may be trained in how to proceed through an expedited protocol to where time and attention is limited. Often the medical emergency is extremely time sensitive, and a first responder may be a law officer who is involved in a dangerous or even hostile situation. For example, a law officer may be involved in an active robbery, shootout, hostage situation, or the like and attention and time to the medical emergency are limited. As disclosed herein, a law officer may call into a dispatch center and verbally convey a series of short, direct phrases to expedite an emergency medical dispatch. The dispatch center includes emergency protocols for either a routine call from an untrained member of the public or expedited emergency protocols from a trained first responder. In other embodiments disclosed herein, a first responder may be trained to use a software application, text messaging, and/or voice messaging in order to communicate with an expedited dispatch protocol of a dispatch center.

As disclosed herein, an expedited dispatch protocol allows a first responder to communicate with a dispatch center and provide patient (or other) information related to the incident with little or no prompting from a dispatcher. The priority dispatch protocol processes the information and generates a determinant code which indicates the priority and type of the emergency response. Accordingly, uniform and consistent results are achieved through the disclosed system and variance due to human subjectivity is minimized. The term "Advanced SEND" may be used to identify the application which incorporates the expedited dispatch protocol.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

A medical dispatch system disclosed herein may be computer implemented in whole or in part on a digital computer. The digital computer includes a processor performing the required computations. The computer further includes a memory in electronic communication with the processor for storing a computer operating system. The computer operating systems may include MS-DOS, Windows, Unix, AIX, CLIX, QNX, OS/2, and Apple. Alternatively, it is expected that future embodiments will be adapted to execute on other future operating systems. The memory also stores application programs including a Computer Aided Dispatch (CAD) program, an emergency medical dispatch protocol, and a user interface program, and data storage. The computer further includes an output device, such as a display unit, for viewing the displayed instructions and inquiries and as a user input device for inputting response data.

Referring to FIG. 1, one embodiment of a computer-aided medical emergency response system 100 is shown. At a dispatch center 102, a dispatcher 104 operates a computer 106 having a memory 108 with an emergency dispatch protocol 110 at least partially stored thereon to enable the dispatcher 104 to rapidly and consistently initiate a medical emergency response. The medical emergency response utilizes medical personnel with appropriate training and a service vehicle with support equipment and medicines on board. A patient 112 may be matched with a suitably equipped vehicle and appropriately trained medical personnel if the resources are available.

The emergency dispatch protocol 110 may be initiated when the dispatcher 104 receives a call from an information provider 114 regarding a medical emergency on behalf of the patient 112. A call coming into the dispatch center 102 may be on an administration line, a 911 telephone call, or through radio. In other cases, the emergency dispatch protocol may be initiated when the computer 106 receives information (other than a phone call) from an information provider 114. In some instances, the patient 112 may call or send information on his or her own behalf.

The emergency dispatch protocol 110 provides a logic tree with questions, possible responses from the information provider 114, and possible instructions to the information provider 114. The information provider responses in some cases lead to subsequent questions and/or instructions to the information provider 114. The responses are processed according to predetermined logic to provide a medical emergency response. During the emergency dispatch protocol 110, the dispatcher 104 and/or the emergency dispatch protocol 110 will gather, inter alia, conditions and circumstances of the medical emergency and the patient's condition, either as presented or as discovered through interrogation, in order to dispatch an appropriate medical emergency response. The emergency dispatch protocol 110 facilitates uniform and consistent gathering of information relating to the emergency. The dispatch may be determined, in part, through a system of logically assigning determinant codes as the protocol progresses (i.e., traverses) through the logic tree. The logic tree of the emergency dispatch protocol 110 may be provided across multiple sub-components of the emergency dispatch protocol 110, including, but not limited to, the case entry protocol 134, the interrogative dispatch protocol 132, and/or the expedited dispatch protocol 116.

Exemplary embodiments of medical dispatch protocols with logic trees are disclosed in U.S. Pat. Nos. 5,857,966, 5,989,187, 6,004,266, 6,010,451, 6,053,864, 6,076,065, 6,078,894, 6,106,459, 6,607,481, 7,106,835, 7,645,234, 8,066,638, 8,103,523, 8,294,570, 8,335,298, 8,355,483, 8,396,191, 8,488,748, 8,670,526, 8,712,020, 8,873,719, 8,971,501, 9,319,859, 9,491,605, and 9,516,166 which are incorporated herein by reference.

The computer 106 further includes the case entry protocol 134 which may act to collect initial information that is relevant to all types of emergencies to which the dispatch center 102 may need to respond. The case entry protocol 134 may also help facilitate decisions as to whether the interrogative dispatch protocol 132 or the expedited dispatch protocol 116 will be used going forward.

The computer 106 further includes an interrogative dispatch protocol 132. The interrogative dispatch protocol 132 may include preprogrammed inquiries that the dispatcher 104 may ask the information provider 114 in order to receive relevant information about an incident. The interrogative dispatch protocol 132 is intended for untrained responders who may require inquiry or prompt from the dispatcher 104 in order to provide the dispatch center 102 with relevant incident information (e.g., the responses by the information provider 114 to the preprogrammed inquiries).

The computer 106 further includes an expedited dispatch protocol 116 to expedite receipt of critical data and emergency dispatch. The expedited dispatch protocol 116 is intended for trained first responders who can provide predetermined, critical data without inquiry or prompt from the dispatcher 104. This incident information may come in the form of pre-scripted inputs known to the dispatch center 102 and the first responder. The first responder may be associated with police, security, military, or a state or federal agency. The expedited dispatch protocol 116 provides the dispatcher 104 with entry fields for the incident information (e.g., the pre-scripted inputs provided by the information provider 114) to allow expedited entry and processing.

The emergency dispatch protocol 110 includes and operates a determinant code calculator 118 to calculate a determinant code from the information provider's responses to preprogrammed inquiries and/or provided pre-scripted inputs. After processing this information, the determinant code calculator 118 generates a determinant code that indicates the urgency of the emergency. The protocol decision points deal directly with life-and-death decisions, and the protocols discussed herein pass a rigorous medical review by a panel of doctors and Emergency Medical Services (EMS) public safety experts who specialize in medical dispatch. The determinant codes may range, for example, from DELTA for generally very serious emergencies to ALPHA for generally less serious emergencies. When a determinant value is identified in one of the four levels (ALPHA—A, BRAVO—B, CHARLIE—C, and DELTA—D) the response configuration (e.g., the 3 medical vehicles involved and the mode of response) is dispatched as indicated by the emergency dispatch protocol 110. If the emergency dispatch protocol 110 or the expedited dispatch protocol 116 determines that the medical emergency is not urgent, a request may be sent to a non-emergency provider instead of dispatching an emergency response vehicle.

As many reported incidents are not urgent medical emergencies, emergency responses are prioritized according to need and available resources. Reported incidents that are urgent emergencies receive a higher priority and merit immediate evaluation and response. If the medical emergency is not urgent then lights and siren are not needed and will not be used, thereby increasing the safety of all those on the road and in the emergency vehicles. While many medical emergencies are not urgent, all responses can benefit from evaluation and the appropriate provision of post-dispatch or pre-arrival instructions. In some embodiments, prior to the arrival of the response, the emergency dispatch protocol 110 or expedited dispatch protocol 116 may provide instructions that are appropriate to the medical emergency such as the physical condition of the patient, the mental condition of the patient, medicinal needs for the patient, medical equipment needs for the patient, physical assistance needs for the patient, and the like.

The determinant code provides a categorization code of the type and level of the incident. The code is provided to a Computer Aided Dispatch (CAD) system 120 for processing. The CAD system 120 is a tool used by dispatchers to track and allocate emergency response resources. The CAD system 120 may manage dispatcher tools for processing emergency calls, including but not limited to the emergency dispatch protocol 110 or the expedited dispatch protocol 116, communication resources (e.g. radio system, alpha pager), mapping tools (e.g., global positioning system (GPS) technology, geographic information systems (GIS)), and vehicle location systems (e.g., automatic vehicle location (AVL)), The CAD system 120 may operate in whole or in part on a separate computer in communication with the computer 106. The primary information used in this task is location information of both the incident and units, unit availability, and the type of incident. CAD systems may use third-party solutions, such as E-911, vehicle location transponders, and mobile data terminals (MDTs) for automating the location and availability tasks.

The computer 106 may include a reporting module 122 to statistically measure the performance of individual staff and overall center performance. The statistics may include compliance rates, call processing statistics, and peer measurements. Once the call is complete, the dispatcher 104 may close the case, and a case summary may be saved, The case summary may be retrieved later for review and/or analysis. The reporting module 122 may determine statistics from the case summaries and/or while the cases are open.

The computer 106 may include a network interface 130 to send information to and receive information from one or more devices that may be external to the computer 106, These external devices may include other devices of the dispatch center 102 (e.g., the CAD system 120 and/or the telephone equipment 124) and may also include devices outside the dispatch center 102 (e.g., the phone 136 or other device, such as a laptop computer, used by the information provider 114). The network interface 130 may be connected to one or more networks of any size, such as the Internet and/or a Local Area Network (LAN) associated with the dispatch center 102 in order to facilitate information transfer between the computer 106 and these one or more external devices. By way of example, there may be a network connecting and facilitating information transfer between the computer 106, the CAD system 120, and one or more service vehicles and/or other units that may be dispatched to the location of the patient 112 in response to an incident. This network may also connect and facilitate information transfer between any or all of these devices and other devices, such as the telephone equipment 124 of the dispatch center 102 and/or the phone 136 of the information provider 114.

The dispatch center 102 includes telephone equipment 124, an input device 126, and an output device 128 to respond to calls and interface with the computer 106. The dispatcher 104 receives calls on the telephone equipment 124, identifies a call as requiring medical attention and initiates the emergency dispatch protocol 110. In identifying the medical emergency the dispatcher 104 asks a series of questions, and while some questions are intuitive some protocol questions may be missed if the dispatcher 104 is not guided. The emergency dispatch protocol 110 provides instructions that are expertly drafted to assist a novice information provider in determining patient needs and condition to thereby provide a suitable medical response. The emergency dispatch protocol 110 may also provide expertly drafted first aid instructions to assist the information provider 114 prior to the arrival of emergency responders.

Figure 2:
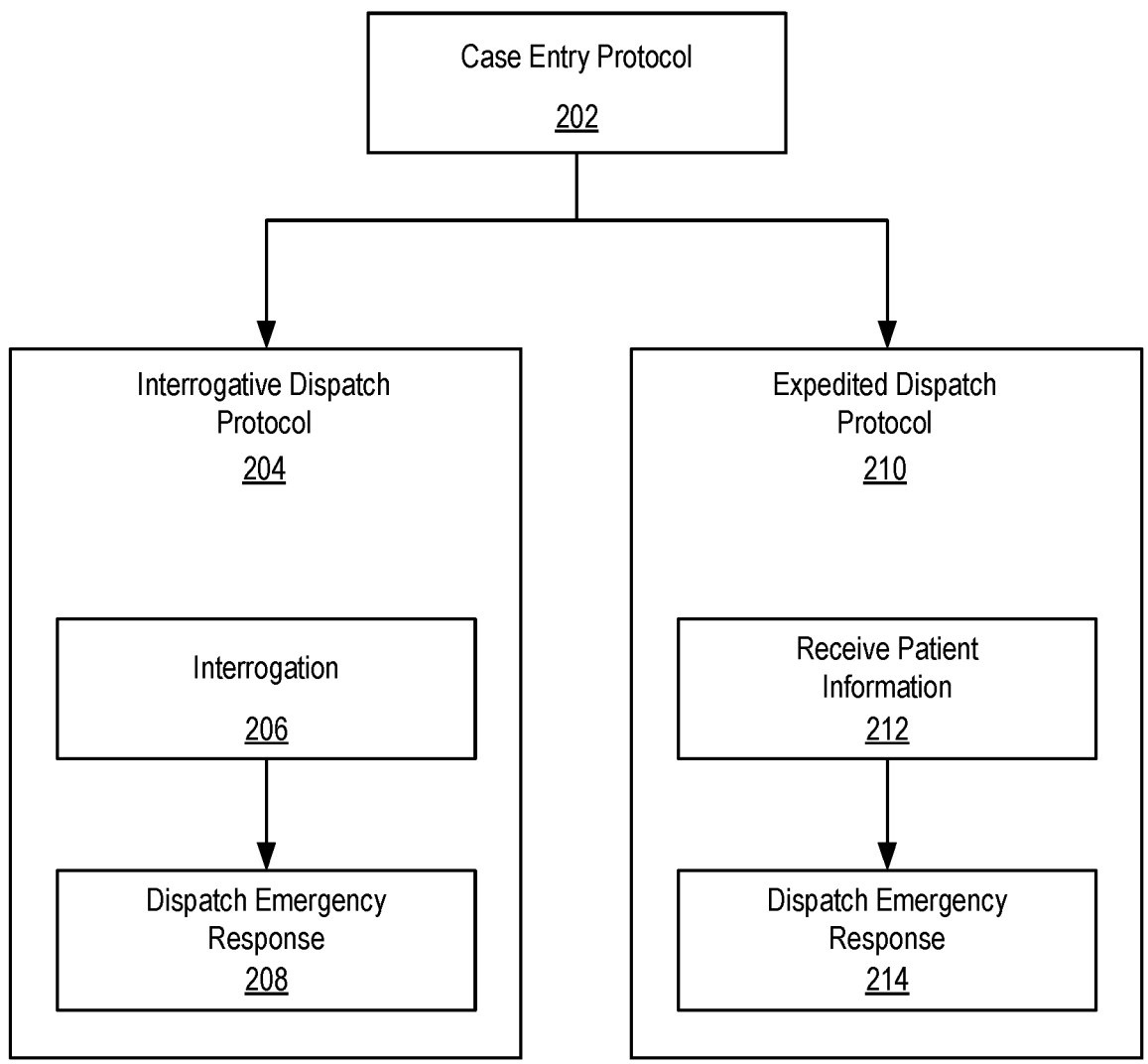
FIG. 2 is a flow diagram of a dispatch protocol system and method, according to one embodiment.

FIG. 2 is a flow diagram 200 illustrating the processing of an incoming emergency call to the dispatch center 102 according to one embodiment of an emergency dispatch protocol 110 of the present disclosure. An incoming emergency call may begin with a case entry protocol 202 that guides the dispatcher 104 in gathering initial information. One aim of the case entry protocol 202 may be to obtain sufficient information from the information provider 114 to confirm the location of the medical emergency, the telephone number of the information provider 114, and a description of the medical problem of the patient 112. It may be that all calls are processed through the case entry protocol 202 to gather initial information. The case entry protocol 202 may include the patient location, information provider telephone number, description of the medical problem of the patient, patient age, patient gender, and any medical issues or complaints. In one embodiment, the case entry protocol 202 may include what is referred to in the field of art as "the four commandments of emergency medical dispatching": the patient's age, the status of the patient's breathing, the status of the patient's consciousness, and a description of the patient's medical condition or chief complaint, if any.

If the case entry protocol 202 determines that the information provider 114 is a member of the general public, then the process continues to the interrogative dispatch protocol 204 which guides the dispatcher 104 by traversing the logic tree of the emergency dispatch protocol 110 using preprogrammed inquiries. The traversal of the logic tree using preprogrammed inquiries may be identified as an interrogation 206 to determine the nature of the medical emergency and, if merited, provide pre-arrival instructions. After determining the nature of the medical emergency, the interrogative dispatch protocol 204 activates the determinant code calculator 118 to generate a determinate code and to dispatch 208 an emergency response with an appropriate medical vehicle and medical personnel.

The pre-arrival instructions can be tailored to the specific situation and/or condition of the patient 112, and may include treatment sequence scripts covering, inter alia, cardiac arrest, choking, and childbirth. For example, the treatment sequence scripts may enable the dispatcher to guide the information provider in CPR, the Heimlich Maneuver, or emergency childbirth procedures. Typically, the result of properly conveyed (by the dispatcher 104) and executed (by the information provider 114) instructions is a more viable patient 112 at the time the emergency responders arrive.

If the case entry protocol 202 determines that the information provider 114 is a first responder then the process routes to the expedited dispatch protocol 210. Confirmation of a first responder may be through a dedicated line, verbal confirmation to the dispatcher 104, and the like. The expedited dispatch protocol 210 receives 212 critical patient information such as identification of a main medical problem or incident type, patient age, conscious state, breathing, chest pain, and severe bleeding. The dispatcher 104 may receive verbal confirmation of the predetermined patient information without asking or prompting the information provider 114. The expedited dispatch protocol 210 may include a list of input fields to receive the patient information as soon as it is spoken by the information provider 114.

Based on the patient information, the expedited dispatch protocol 210 determines the nature of the medical emergency and activates the determinant code calculator 118 to generate a determinate code. The expedited dispatch protocol 210 dispatches 214 an emergency response with an appropriate medical vehicle and medical personnel. The expedited dispatch protocol 210 may also provide pre-arrival instructions to the information provider 114 as previously discussed. The pre-arrival instructions may be directed to a first responder with expected training in first aid and other emergency medical training.

Referring to FIGS. 3A-3H, embodiments of a user interface 300 for the emergency dispatch protocol 110 that are displayed to the dispatcher 104 are shown. In the embodiment of FIG. 3A, the user interface 300 may act to gather information for the case entry protocol 202. In the embodiments of FIGS. 3B-3H, the user interface 300 may act to gather information for the expedited dispatch protocol 210 subsequent to the identification by the case entry protocol 202 that the information provider 114 is a first responder. One of skill in the art will appreciate that the user interface 300 may be embodied in various formats and are all within the scope of the invention.

In FIG. 3A, the user interface 300 provides input fields for the location of the patient 302, the telephone number of the information provider 304, the information provider's problem description 306, whether the information provider is with the patient 308, how many are hurt or sick 310, the patient's age 312, the patient's gender 314, if the patient is conscious 316, if the patient is breathing 318, and a chief complaint code 320.

The chief complaint code provided to the dispatcher 104 may be used in industry practice and its receipt/usage may instruct the dispatcher 104 and/or the computer 106 to proceed with an expedited priority dispatch. The information provider 114 may verbally confirm to the dispatcher 104 that the information provider 114 is a first responder and prepared to provide unprompted patient information. The dispatcher 104 may enter such known chief complaint code into the user interface 300 to activate the expedited dispatch protocol 210. In the illustrated embodiment, the Chief Complaint Code is entered as "38" which is used to execute the "Advanced SEND" protocol. The "Advanced SEND" protocol, shown in the user interface 300, is also referred to herein as the expedited dispatch protocol 210.

At any time during the case entry protocol 202, the information provider 114 who is a caller may verbally confirm to the dispatcher 104 and/or the computer 106 that the information provider 114 is a first responder. The information provider 114 may also call in on, text in on, or otherwise use a dedicated information channel, such as a dedicated line, extension, or radio frequency, the use of which identifies the information provider 114 as a first responder. The information provider 114 may also be identified as a first responder through the communication of the computer 106 with a software application that is known to be operated on a phone 136 or other device associated with the information provider 114 who a first responder, as will be described further below.

The case entry protocol 202 may require entry of the location of the patient 302, the number injured 310, patient age 312, conscious state 316, and breathing state 318 before proceeding. This information may be provided via interrogation by the dispatcher 104, or it may be that an information provider 114 who is a first responder provides this information without being prompted by the dispatcher 104. Thus, after an information provider 114 is confirmed as a first responder, other input such as the information provider's telephone number, the information provider 114 being with the patient 308, and/or the patient gender 314 may not be needed to proceed.

In FIG. 3B, the user interface 300 prompts the dispatcher 104 to receive the main medical problem or incident type. The user interface 300 may provide a list of problem categories such as "Injuries (TRAUMA)", "Bleeding (TRAUMA)", "MEDICAL", "Bleeding (non-traumatic)", "Traffic/Transportation incident", "EXCITED DELIRIUM", "Tasered", or "Unknown". Each of the categories shown in this list (and in similar lists described throughout) may be a pre-scripted input of an expedited dispatch protocol and known to the dispatcher 104 and the information provider 114. Further, the specific arrangement of the categories as shown in this list (and in similar lists described throughout) are given by way of example and not by way of limitation. Other lists with categories or other items other than what has been expressly presented herein are contemplated.

The dispatcher 104 may highlight and select any one of the problem categories. The information provider 114 may verbally identify the main medical problem or incident type without being prompted by the dispatcher 104. In FIG. 3B, the problem category is identified as being "Injuries (TRAUMA)".

FIG. 3B (and other FIGS. throughout) shows an embodiment of the contents of "Additional Information" field 321. This field may contain information to help the dispatcher 104 appropriately respond to queries that may be presented by the user interface 300. The "Additional Information" field 321 may be displayed by default prior to the selection of, e.g., the problem category by the dispatcher 104 (or by default prior to another input by the dispatcher 104). Alternatively, the dispatcher 104 may have previously selected the associated "Additional Information" tab 323 in order to display the "Additional Information" field 321.

In FIG. 3C, the user interface 300 prompts the dispatcher 104 to receive the type of injuries/incident. The user interface 300 may provide an option to select "NOT DANGEROUS body area", "POSSIBLY DANGEROUS body area", "Chest", "Neck", "Head", "Fall (ground level)", "MINOR hemorrhage", "Minor injuries", or "Critical injuries". As indicated, "POSSIBLY DANGEROUS body area" is selected.

FIG. 3C (and other FIGS. throughout) shows an embodiment of a "Question Answers" field 322. The "Question Answers" field 322 may be displayed automatically in response to the selection of the main medical problem category (or other selections described herein) by the dispatcher 104, as described relative to FIG. 3B above. Alternatively, the dispatcher 104 may have selected the associated "Question Answers" tab 325 in order to display the "Question Answers" field 322. The "Question Answers" field 322 is updated with the answer to the previous prompt as the protocol proceeds.

In FIG. 3D, the user interface 300 prompts the dispatcher 104 as to whether the patient 112 is completely alert. The user interface 300 may provide an option to select "Yes", "No", or "Unknown". As indicated, "Yes" is selected. The user interface 300 may provide a "Question Answers" field 322 to list previously entered answers. This provides a visual indicator to the dispatcher 104 and will be saved as a record. As indicated, the problem category is "Injuries (TRAUMA)" and the first responder report that an injury is to a "POSSIBLY DANGEROUS body area". As shown, the "Question Answers" field 322 is updated with the answer to the previous prompt as the protocol proceeds.

In FIG. 3E, the user interface 300 prompts the dispatcher 104 as to whether the patient 112 is having difficulty breathing. The user interface 300 may provide an option to select "No", "Yes", or "Unknown". As indicated, "Yes" is selected. As shown, the "Question Answers" field 322 is updated with the answer to the previous prompt as the protocol proceeds.

In FIG. 3F, the user interface 300 prompts the dispatcher 104 as to whether the patient 112 is seriously bleeding. The user interface 300 may provide an option to select "No bleeding now"; "Yes, SERIOUS"; "Unknown"; or "Bleeding, not serious". As indicated, "No bleeding now" is selected.

In FIG. 3G, the user interface 300 prompts the dispatcher 104 as to the request of the specific response mode. The first responder is aware of the environment and conditions regarding the medical emergency and is in a better situation to determine the type of response. For example, the first responder may be in a hostile crowd situation or in an active hostage situation where a lights-and-siren situation may aggravate conditions. In one situation, although a high priority may be assigned to an emergency response, the response may come in without the lights and siren as the response vehicle approaches the vicinity. The user interface 300 may provide an option to select "No", "HOT (lights-and-siren)", or "COLD (routine)". If the information provider 114 provides no preference, the dispatcher 104 may enter "No", and the expedited dispatch protocol 210 may make the determination based on information pre-programmed into the protocol. Once again, the "Question Answers" field 322 is updated with the answer to the previous prompt as the protocol proceeds.

In FIG. 3H, the user interface 300 provides a summary field 324 which lists the pre-scripted inputs selected by the dispatcher 104. The expedited dispatch protocol 210 activates the determinant code calculator 118 which lists the determinant code as Delta 7. The determinant code may be listed in the send field 326 which prompts the dispatcher 104 to confirm generation of an emergency response. This confirmation may occur when the dispatcher 104 uses the input device 126 to interact with the computer 106 in a specific way (e.g., by using a mouse to click on the send field 326). The user interface 300 may also include a determinants field which displays the various determinant codes 328.

The embodiments of FIGS. 4A-4F illustrate another example of the use of a user interface to gather information for an expedited dispatch protocol such as the expedited dispatch protocol 210. In FIG. 4A, a new case entry has already been made and the user interface 400 now prompts the dispatcher 104 to enter the main medical problem category. The user interface 400 provides a list of problems to facilitate dispatcher selection as soon as the information provider 114 provides the problem. Once again, in using the expedited dispatch protocol 210 it is anticipated that the information provider 114 is a trained first responder who is aware of the pre-scripted inputs and does not need to be prompted. Accordingly, the information provider 114 may quickly convey the pre-scripted inputs and the dispatcher 104 may proceed through the expedited dispatch protocol 210 quickly and save precious time. In the illustrated embodiment of FIG. 4A, the dispatcher 104 has highlighted "Bleeding (TRAUMA)".

In FIG. 4B, the user interface 400 prompts to confirm if the patient 112 is completely alert. The user interface 400 may provide an option to select "Yes", "No", or "Unknown". As indicated, "Yes" is selected. As in the previous embodiment, the user interface 400 may include a "Question Answers" field 402 to list previously entered answers.

In FIG. 4C, the user interface 400 prompts the dispatcher 104 as to whether the patient 112 is having difficulty breathing. The user interface 400 may provide an option to select "No", "Yes", or "Unknown". As indicated, "No" is selected. The "Question Answers" field 402 is updated with the answer to the previous prompt as the protocol proceeds.

In FIG. 4D, the user interface 400 prompts the dispatcher 104 as to the severity of the patient bleeding. The problem has already been identified as bleeding, and the user interface 400 may provide the options of "No", "Yes", "Unknown", or "Insignificant". As indicated, "Yes" is selected in response to the question of whether the blood is spurting or pouring out.

In FIG. 4E, the user interface 400 prompts the dispatcher 104 as to the request of the specific response mode. The user interface 400 provides an option to select "No", "HOT (lights-and-siren)", or "COLD (routine)". As indicated, the "Hot (lights-and-siren)" option is selected.

In FIG. 4F, the user interface 400 provides a summary field 404 which lists the pre-scripted inputs selected by the dispatcher 104. The expedited dispatch protocol 210 activates the determinant code calculator 118 which lists the determinant code as Bravo 2. The determinant code may be listed in the send field 406 which prompts the dispatcher 104 to confirm generation of an emergency response. The user interface 400 may also include a determinants field which displays the various determinant codes 408. As shown, in some embodiments the user interface 400 may also highlight higher determinant codes that may be used to "Override" the calculated determinant code.

The embodiments of FIGS. 5A-5E illustrate another example of the use of a user interface to gather information for an expedited dispatch protocol such as the expedited dispatch protocol 210. In FIG. 5A, the user interface 500 prompts the dispatcher 104 to enter the main medical problem category. In the illustrated embodiment of FIG. 5A, the dispatcher 104 has highlighted "MEDICAL".

In FIG. 5B, the user interface 500 prompts for the type of incident. The user interface 500 may provide an option to select "Chest pain/discomfort", "STROKE", "Seizure", "Other serious illness", or "Minor illness". In the illustrated embodiment of FIG. 5B, the dispatcher 104 has selected "Other serious illness".

In FIG. 5C, the user interface 500 prompts the dispatcher 104 as to whether the patient 112 is having difficulty breathing. The user interface 500 may provide an option to select "No", "Yes", or "Unknown". As indicated, "Yes" is selected. The "Question Answers" field 502 is updated with the answer to the previous prompt as the protocol proceeds.

In FIG. 5D, the user interface 500 prompts the dispatcher 104 to the specific response mode and "No" is selected.

In FIG. 5E, the user interface 500 provides a summary field 504 which lists the pre-scripted inputs selected by the dispatcher 104. The expedited dispatch protocol 210 activates the determinant code calculator 118 which lists the determinant code as Delta 7. The determinant code may be listed in the send field 506 which prompts the dispatcher 104 to confirm generation of an emergency response.

The embodiments of FIGS. 6A-6F illustrate another example of the use of a user interface to gather information for an expedited dispatch protocol such as the expedited dispatch protocol 210. In FIG. 6A, the user interface 600 prompts for a main medical problem category and "Bleeding (non-traumatic)" is selected.

In FIG. 6B, the user interface 600 prompts as to whether the patient 112 is completely alert and "No" is selected.

In FIG. 6C, the user interface 600 prompts as to whether the patient is having difficulty breathing and "No" is selected.

In FIG. 6D, the user interface 600 prompts as to whether the bleeding, previously selected as the problem, is serious. In the illustrated embodiment, "No" is selected.

In FIG. 6E, the user interface 600 prompts the dispatcher 104 to the specific response mode and "No" is selected.

In FIG. 6F, the user interface 600 provides a summary field 602 and illustrates the determinant code Delta 6 in the send field 604.

Figure 7B:
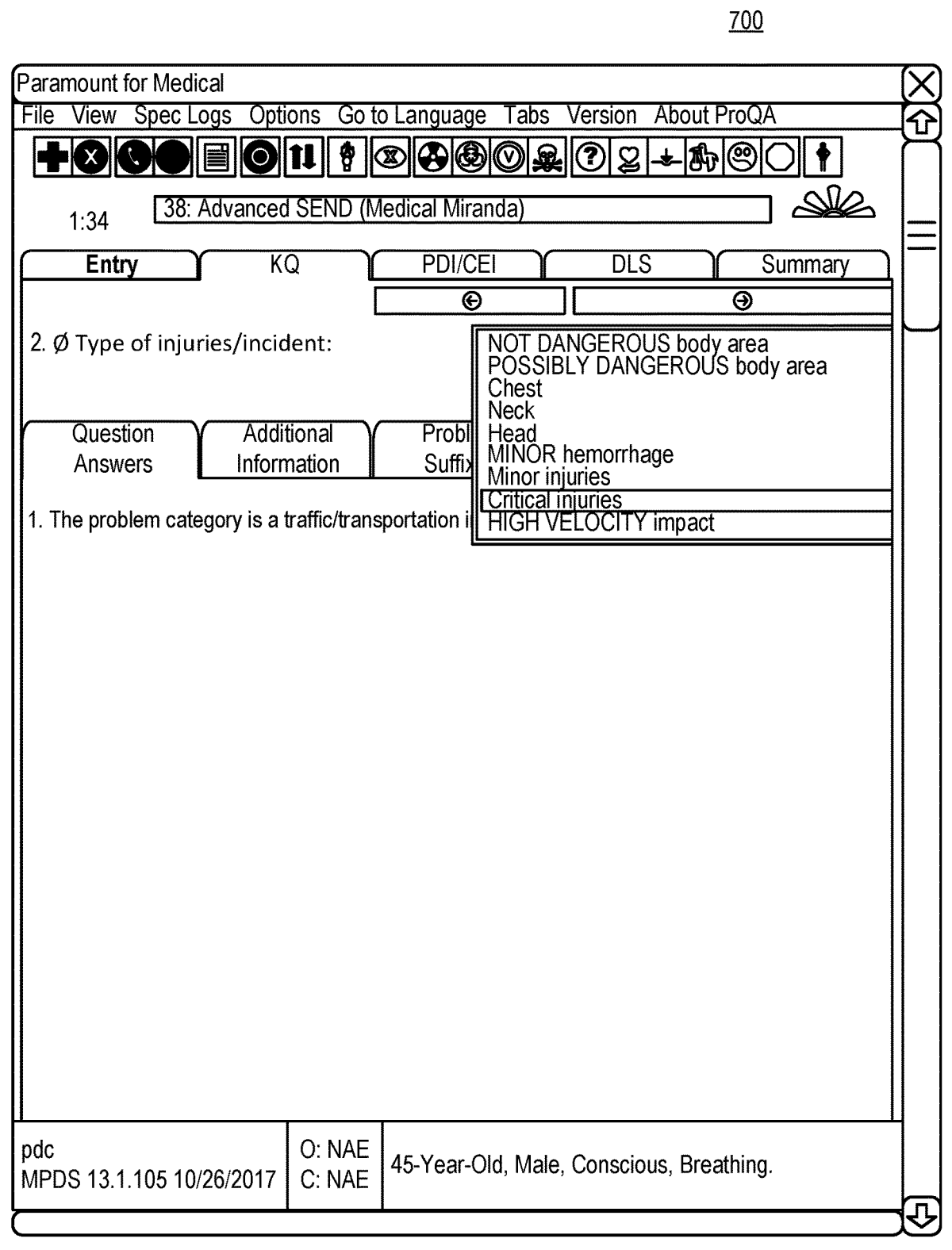

The embodiments of FIGS. 7A-7G illustrate another example of the use of a user interface to gather information for an expedited dispatch protocol such as the expedited dispatch protocol 210. In FIG. 7A, the user interface 700 prompts for a main medical problem category and "Traffic/Transportation incident" is selected.

In FIG. 7B, the user interface 700 prompts as to the type of injury/incident resulting from traffic or transportation and "Critical injuries" is selected.

In FIG. 7C, the user interface 700 prompts as to whether the patient 112 is completely alert and "Yes" is selected.

In FIG. 7D, the user interface 700 prompts as to whether the patient 112 is having difficulty breathing and "Unknown" is selected.

In FIG. 7E, the user interface 700 prompts as to whether the patient is experiencing serious bleeding and "Bleeding, not serious" is selected.

In FIG. 7F, the user interface 700 prompts the dispatcher 104 to the specific response mode and "HOT (lights-and-siren)" is selected.

In FIG. 7G, the user interface 700 provides a summary field 702 and illustrates the determinant code Delta 3 in the send field 704.

The embodiments of FIGS. 8A-8D illustrate another example of the use of a user interface to gather information for an expedited dispatch protocol such as the expedited dispatch protocol 210. In FIG. 8A, the user interface 800 prompts for a main medical problem category and "EXCITED DELIRIUM" is selected.

In FIG. 8B, the user interface 800 prompts as to whether the patient 112 is in protective custody and "No" is selected. As can be seen in the "Questions Answers" field 802, the expedited dispatch protocol may have inferred from the previous selection of "EXCITED DELIRIUM" that the victim is not fully alert, without the need for a report as such from the first responder or entry of such status by the dispatcher 104.

In FIG. 8C, the user interface 800 prompts the dispatcher 104 to the specific response mode and "Cold (routine)" is selected.

In FIG. 8D, the user interface 800 provides a summary field 804 and illustrates the determinant code Delta 1 in the send field 806.

The embodiments of FIGS. 9A-9E illustrate another example of the use of a user interface to gather information for an expedited dispatch protocol such as the expedited dispatch protocol 210. In FIG. 9A, the user interface 900 prompts for a main medical problem category and "Tasered" is selected.

In FIG. 9B, the user interface 900 prompts as to whether the patient 112 is completely alert and "Yes" is selected.

In FIG. 9C, the user interface 900 prompts as to whether the patient 112 is in protective custody and "Yes" is selected.

In FIG. 9D, the user interface 900 prompts the dispatcher 104 to the specific response mode and "COLD (routine)" is selected.

In FIG. 9E, the user interface 900 provides a summary field 902 and illustrates the determinant code Bravo 3 in the send field 904. As shown, in some embodiments the user interface 900 may also highlight higher determinant codes that may be used to "Override" the calculated determinant code.

Figure 10B:
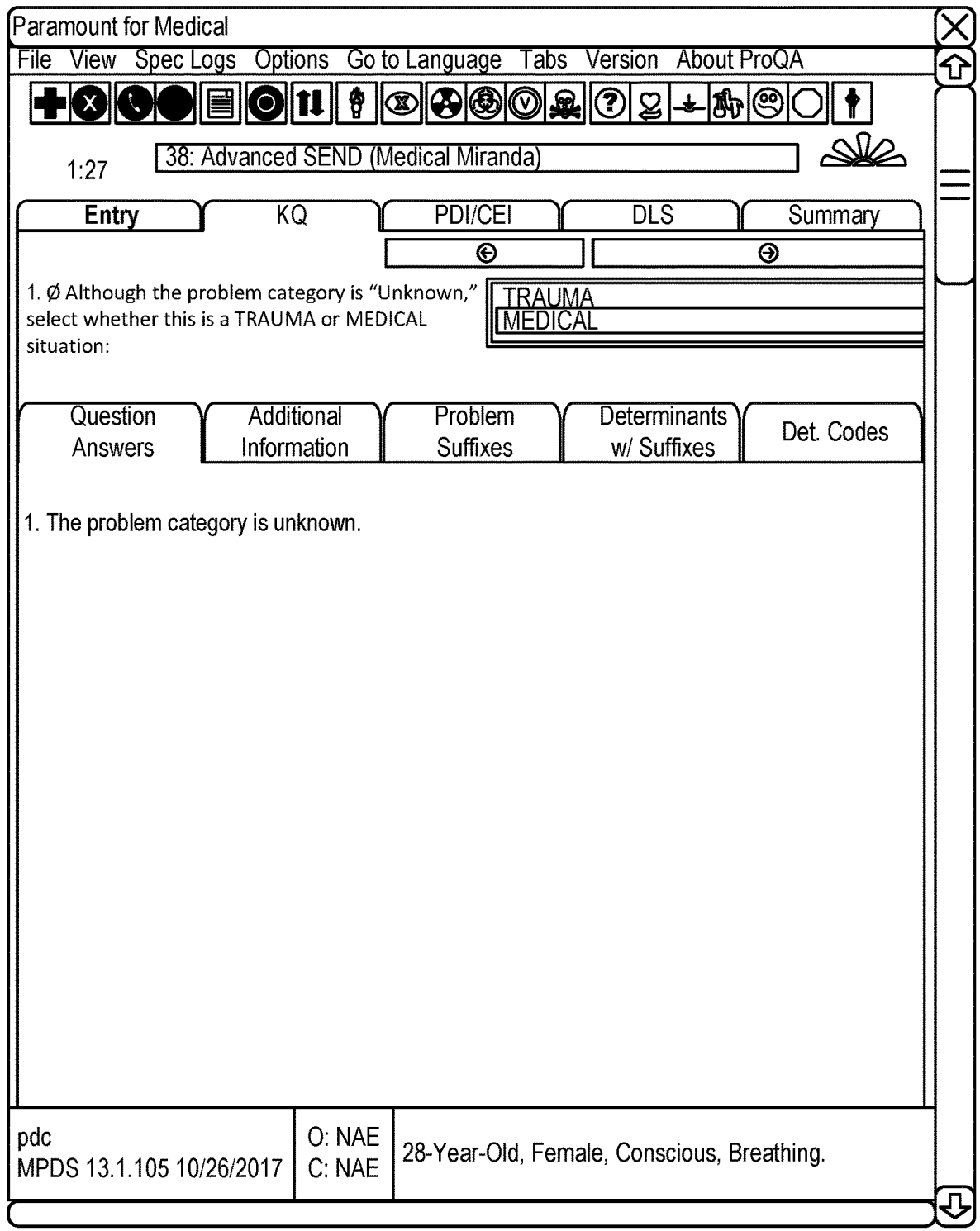

The embodiments of FIGS. 10A-10F illustrate another example of the use of a user interface to gather information for an expedited dispatch protocol such as the expedited dispatch protocol 210. In FIG. 10A, the user interface 1000 prompts for a main medical problem category and "Unknown" is selected.

In FIG. 10B, the user interface 1000 prompts as to whether the problem category is trauma or medical and "MEDICAL" is selected.

In FIG. 10C, the "Question Answers" field 1002 confirms that this is a medical situation, the user interface 1000 prompts as to whether the patient 112 is completely alert, and "No" is selected.

In FIG. 10D, the user interface 1000 prompts to confirm if the patient 112 is having difficulty breathing and "No" is selected.

In FIG. 10E, the user interface 1000 prompts the dispatcher 104 to the specific response mode and "Hot (lights-and-siren)" is selected.

In FIG. 10F, the user interface 1000 provides a summary field 1004 and illustrates the determinant code Delta 6 in the send field 1006.

As demonstrated in FIGS. 3B-10E, the expedited dispatch protocol 210 prompts for different input depending on the initial problem category. Thus, the expedited dispatch protocol 210 navigates different paths through the logic tree of the emergency dispatch protocol 110 depending on the problem, incident, or chief complaint.

Referring to FIGS. 11A and 11B, the front and back of an "Advanced SEND" card 1100 is shown. The card 1100 may be carried by a first responder information provider 114 as a reminder for the pre-scripted input that is to be relayed to the dispatcher 104. In proceeding through the different problems or incidents, the card 1100 lists the necessary pre-scripted inputs. Although it is expected that first responders are trained as to the pre-scripted input, the card 1100 provides a quick visual reminder. As can be appreciated, in highly stressful situations, a first responder may benefit from a visual reminder. The first responder information provider 114 provides the pre-scripted input listed on the card 1100 without waiting for dispatcher queries. Should a first responder hesitate or fail to provide a pre-scripted input, the expedited dispatch protocol 210 provides a visual indication to the dispatcher 104 who can query for that input.

Uses of the emergency dispatch protocol 110 not involving telephone calls will now be discussed.

FIGS. 12A-12H illustrate embodiments of a user interface of a software application for use with the emergency dispatch protocol 110. A smartphone 1202 displays a user interface 1204 of a software application that may communicate with the emergency dispatch protocol 110 of the dispatch center 102. The smartphone may be the phone 136 of FIG. 1. The software application may communicate with the computer 106 of the dispatch center 102 via the network interface 130 to receive prompts and provide responses to the emergency dispatch protocol 110 without dispatcher 104 acting to provide the prompts or to enter the responses. The software application may be used by, e.g., an information provider 114 who is a first responder who is with a victim.

Figure 12B:
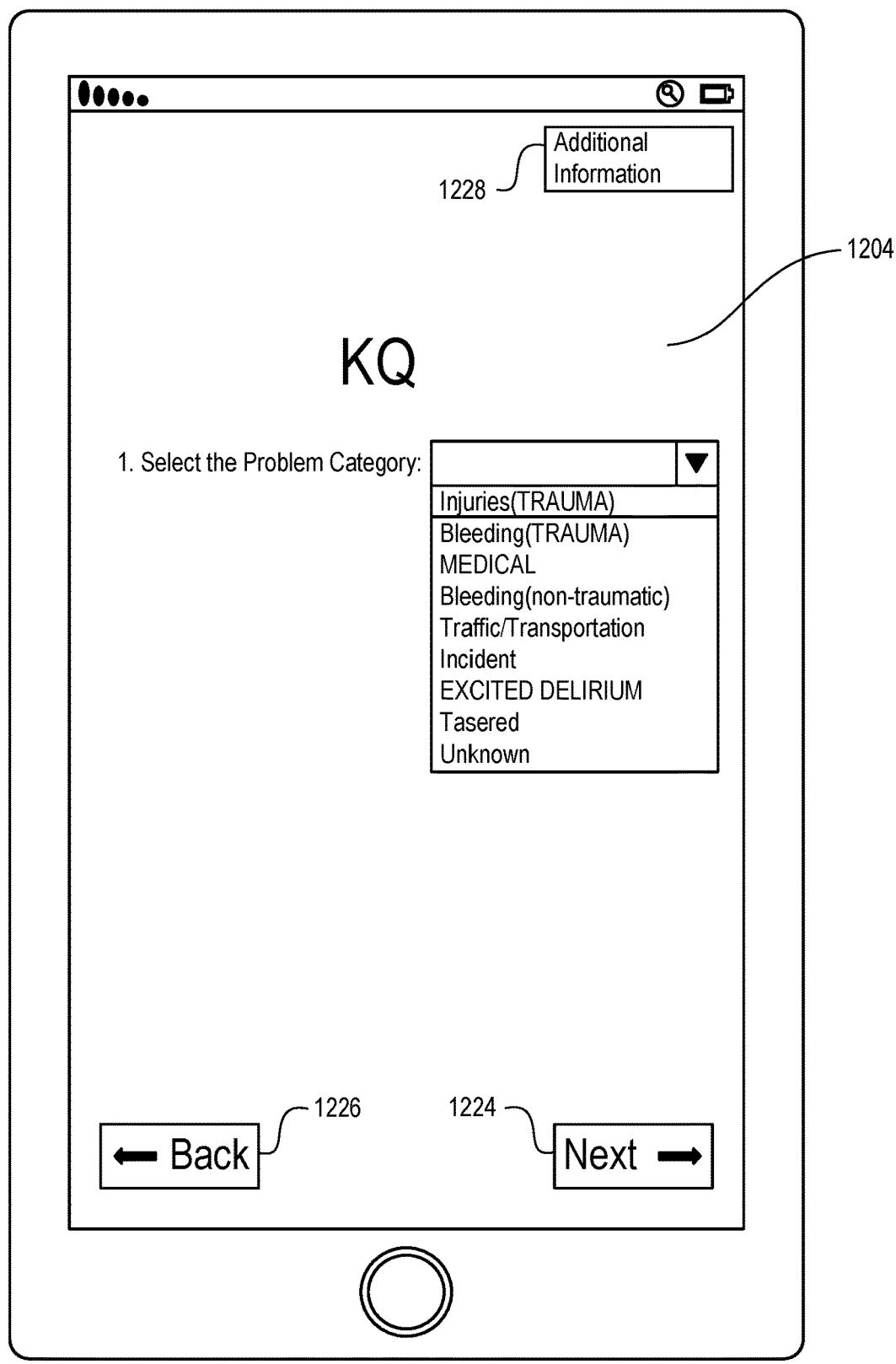

In FIG. 12A, the user interface 1204 prompts the information provider 114 to provide initial information regarding the emergency to the software application. This initial information may include information that would be gathered via the case entry protocol 202 for processing an incoming emergency call to a dispatch center 102. It may correspond to, e.g., the fields discussed in relation to FIG. 3A above. In the embodiment of 12A, the user interface 1204 provides input fields for the location of the patient 1206, the telephone number of the information provider 1208, the information provider's problem description 1210, whether the information provider is with the patient 1212, how many are hurt or sick 1214, the patient's age 1216, the patient's gender 1218, if the patient is conscious 1220, and if the patient is breathing 1222. In the specific embodiment of FIG. 12A, it is assumed that the user of the software application is a first responder that intends to activate the expedited dispatch protocol 210, and therefore the chief complaint code field is therefore not presented to the user. Other embodiments where this field may be used (e.g., where the information provider 114 using the software application is not a trained first responder) are contemplated. Throughout embodiments of FIG. 12, the "Next" button 1224 may give the information provider 114 the option to go forward to a next screen to continue entering information, where the screens may further be ordered in the order presented in FIGS. 12A-12G.

In FIG. 12B, the user interface 1204 begins receiving input from the information provider 114 corresponding to the information needed by the expedited dispatch protocol 210 of the dispatch center 102. The user interface 1204 may provide a text prompt and a drop-down box that, when selected, presents a selectable list of main medical problem categories such as "Injuries (TRAUMA)", "Bleeding (TRAUMA)", "MEDICAL", "Bleeding (non-traumatic)", "Traffic/Transportation incident", "EXCITED DELIRIUM", "Tasered", or "Unknown". The information provider 114 may select on one of the problem categories. In FIG. 12B, the problem category is identified as being "Injuries (TRAUMA)". Throughout embodiments of FIG. 12, the "Back" button 1226 may give the information provider 114 the option to go back to a previous screen should the information provider 114 wish to change any information on a previous screen. As before, the "Next" button 1224 may give the information provider 114 the option to go forward to a next screen to continue entering information.

FIG. 12B (and additional FIGS. herein) illustrates an "Additional Information" button 1228 on the user interface 1204 of the software application of the smartphone 1202. This button may open information to help the information provider 114 appropriately respond to queries that may be presented by the user interface 1204. This screen may display, e.g., the same (or substantially similar) information as what is contained on the "Additional Information" tab discussed in more detail in relation to FIG. 3B above.

Figure 12C:
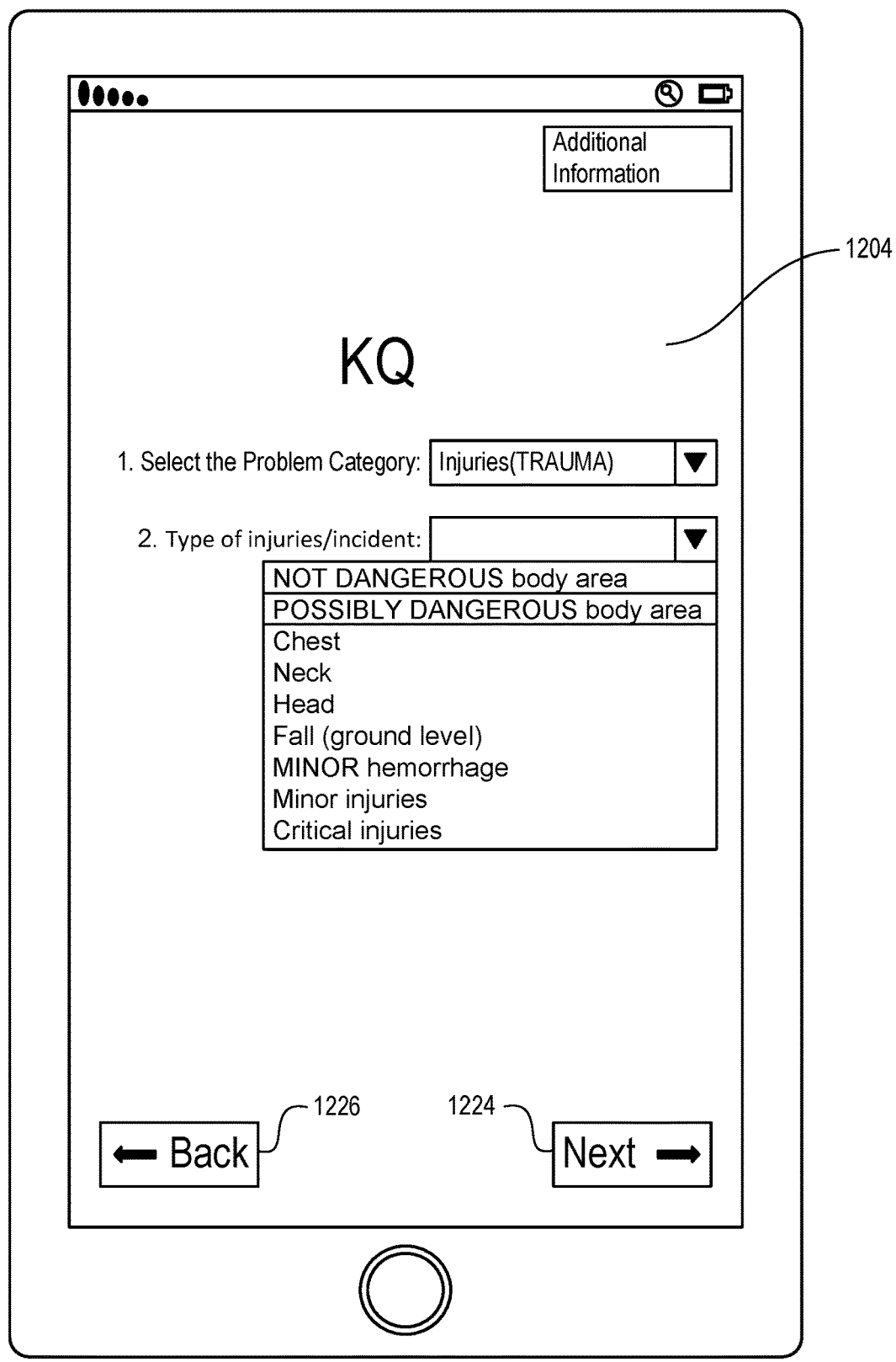

In FIG. 12C, the user interface 1204 prompts the information provider 114 to input the type of injuries/incident. Once the corresponding drop-down box is selected, the user interface 1204 may provide an option to select "NOT DANGEROUS body area" "POSSIBLY DANGEROUS body area", "Chest", "Neck", "Head", "Fall (ground level)", "MINOR hemorrhage", "Minor injuries", or "Critical injuries". As indicated, "POSSIBLY DANGEROUS body area" is selected. As shown, the user interface 1204 may retain the previous prompt and response on the screen and add the new prompt and drop-down box to the bottom of the of the previous prompt and response. As before, the "Next" button 1224 and the "Back" button 1226 give the information provider 114 the option to traverse the various screens.

Figure 12D:
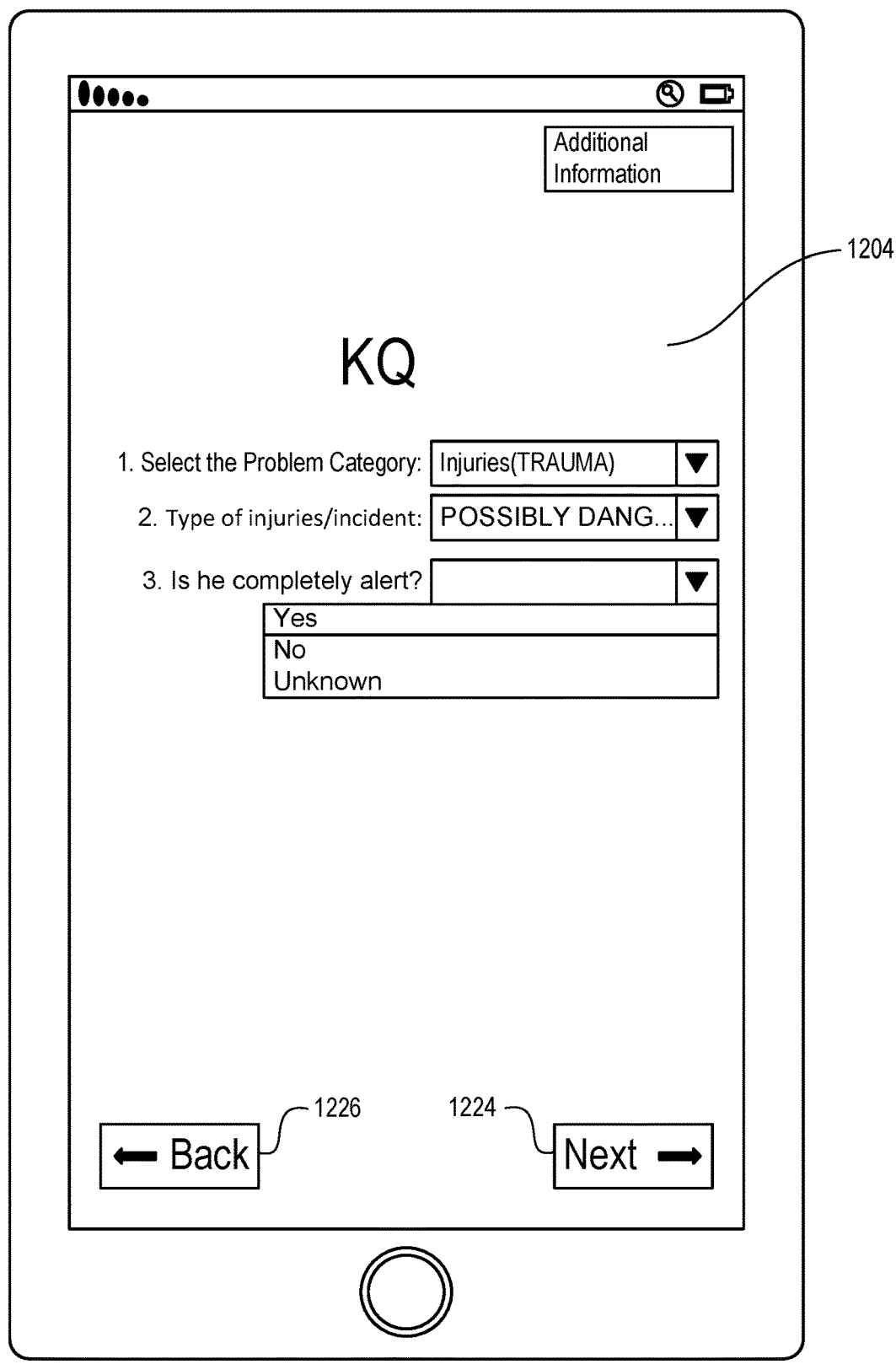

In FIG. 12D, the user interface 1204 prompts the information provider 114 as to whether the patient 112 is completely alert. Once the corresponding drop-down box is selected, The user interface 300 may provide an option to select Yes, No, or Unknown. As indicated, "Yes" is selected. As shown, the user interface 1204 may continue to retain the previous prompts and responses on the screen and add the new prompt and drop-down box to the bottom of these previous prompts and responses. As before, the "Next"

button 1224 and the "Back" button 1226 give the information provider 114 the option to traverse the various screens.

Figure 12E:
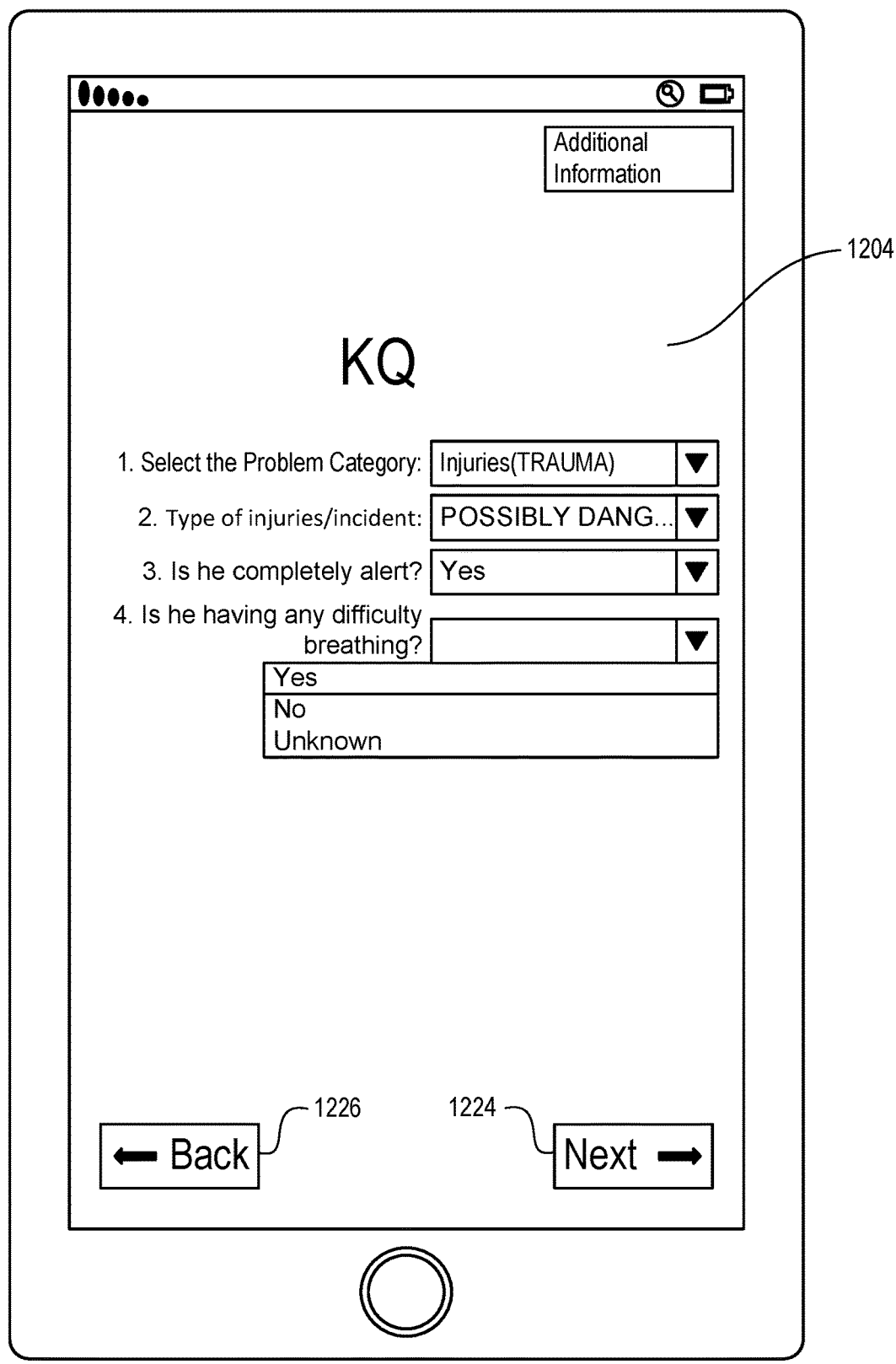

In FIG. 12E, the user interface 1204 prompts the information provider 114 as to whether the patient 112 is having difficulty breathing. Once the corresponding drop-down box is selected, the user interface 1204 may provide an option to select "No", "Yes", or "Unknown". As indicated, "Yes" is selected. As shown, the display of the new prompt and drop-down box beneath the previous prompts and responses continues. As before, the "Next" button 1224 and the "Back" button 1226 give the information provider 114 the option to traverse the various screens.

Figure 12F:
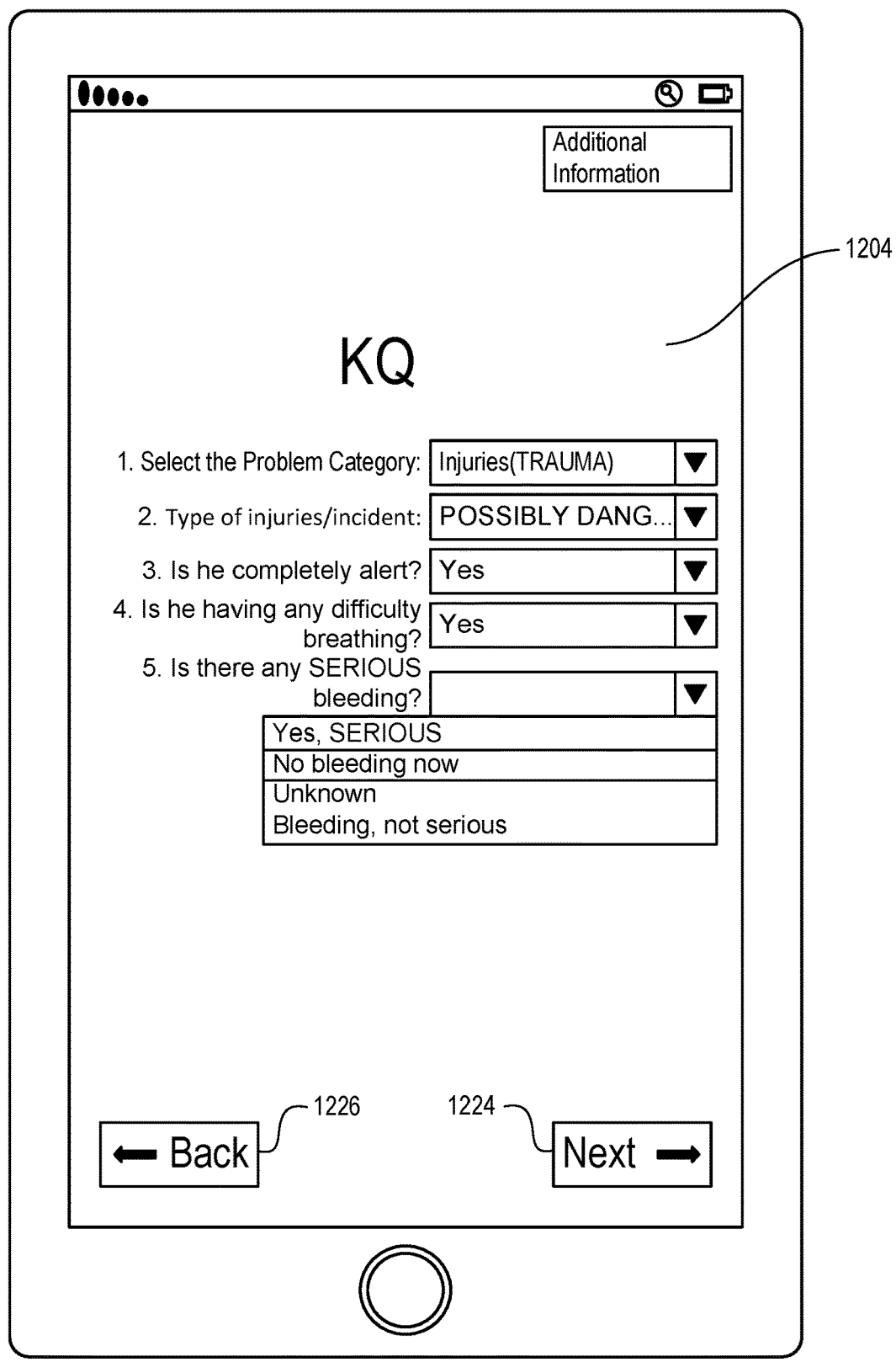

In FIG. 12F, the user interface 1204 prompts the information provider 114 as to whether the patient 112 is seriously bleeding. Once the corresponding drop-down box is selected, the user interface 1204 may provide an option to select "No bleeding now"; "Yes, SERIOUS"; "Unknown"; or "Bleeding, not serious". As indicated, "No bleeding now" is selected. As shown, the display of the new prompt and drop-down box beneath the previous prompts and responses continues. As before, the "Next" button 1224 and the "Back" button 1226 give the information provider 114 the option to traverse the various screens.

Figure 12G:
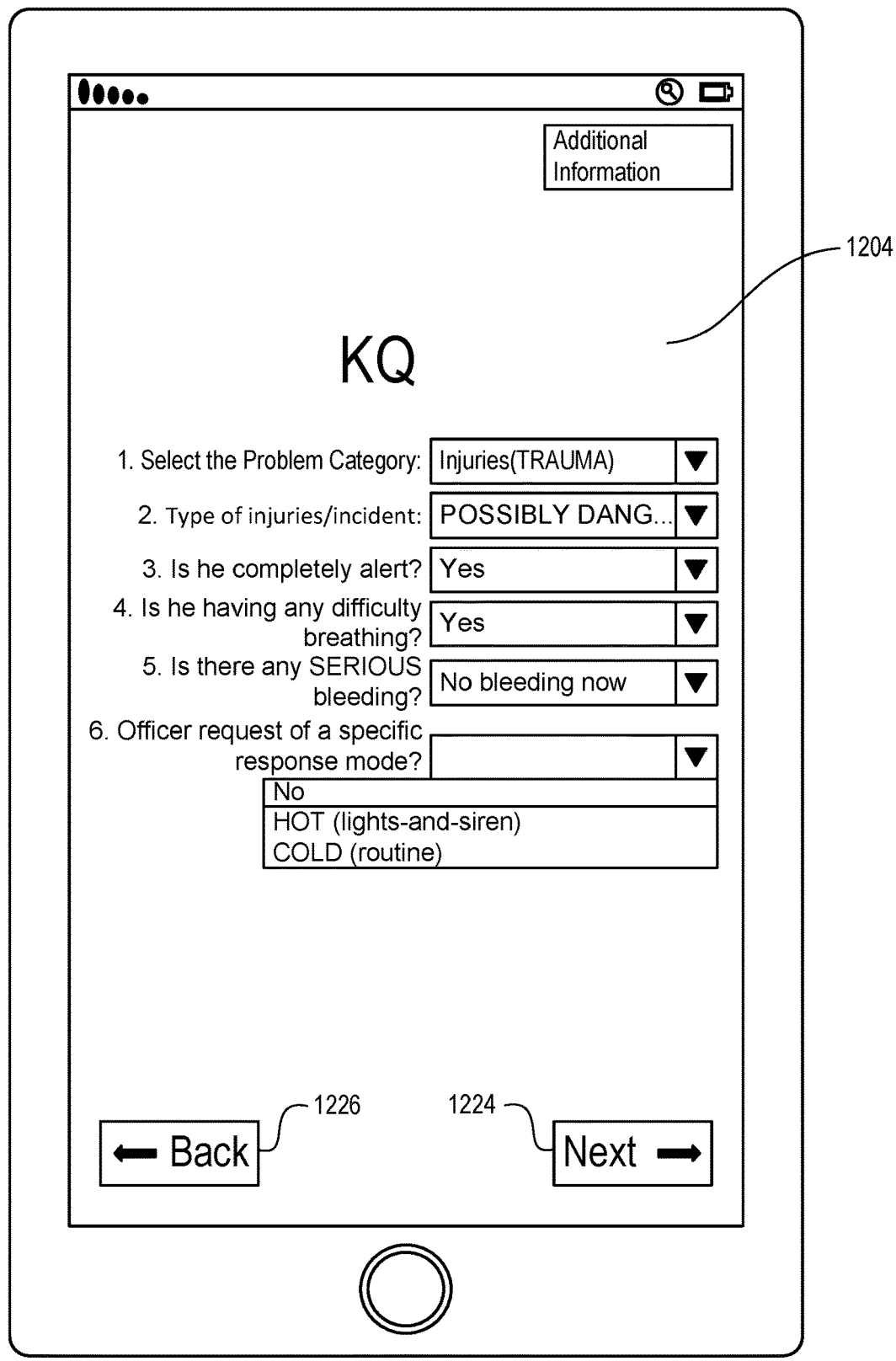

In FIG. 12G, the user interface 1204 prompts the information provider 114 as to the request of the specific response mode. Once the corresponding drop-down box is selected, the user interface 1204 may provide an option to select "No", "HOT (lights-and-siren)", or "COLD (routine)". As indicated, "No" is selected. As shown, the display of the new prompt and drop-down box beneath the previous prompts and responses continues. As before, the "Next" button 1224 and the "Back" button 1226 give the information provider 114 the option to traverse the various screens.

Figure 12H:
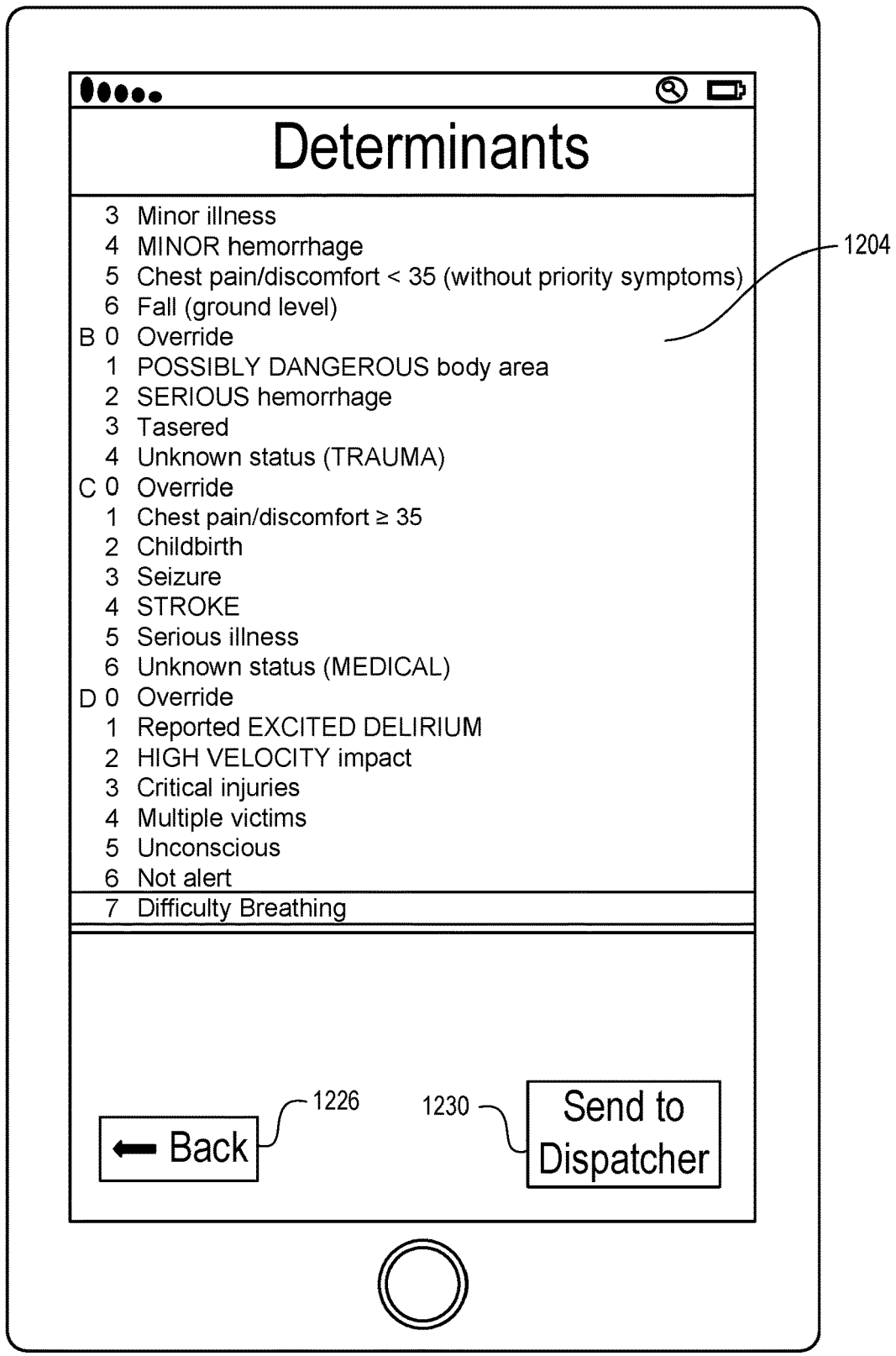

In FIG. 12H, the user interface 1204 now displays "Send to Dispatcher" button 1230, which may act to provide the information gathered as described in relation to FIGS. 12A-12G to the computer 106 of the dispatch center 102 via the network interface 130. By pressing the "Send to Dispatcher" button 1230, the information provider 114 may also signal to the computer 106 to use the provided information with the determinant code calculator 118 to generate a determinant code and alert the dispatcher 104. As shown in the embodiment of FIG. 12H, the user interface 1204 may also be equipped to show a projected determinant code that will likely be used by the dispatcher 104 when they receive the information that has been collected as described in FIGS. 12A-12G from the information provider 114. As before, the "Back" button 1226 gives the information provider 114 the option to return to the prior screens. Use of this sent information after it is received by the computer 106 of the dispatch center 102 will be described further below.

Figure 13:
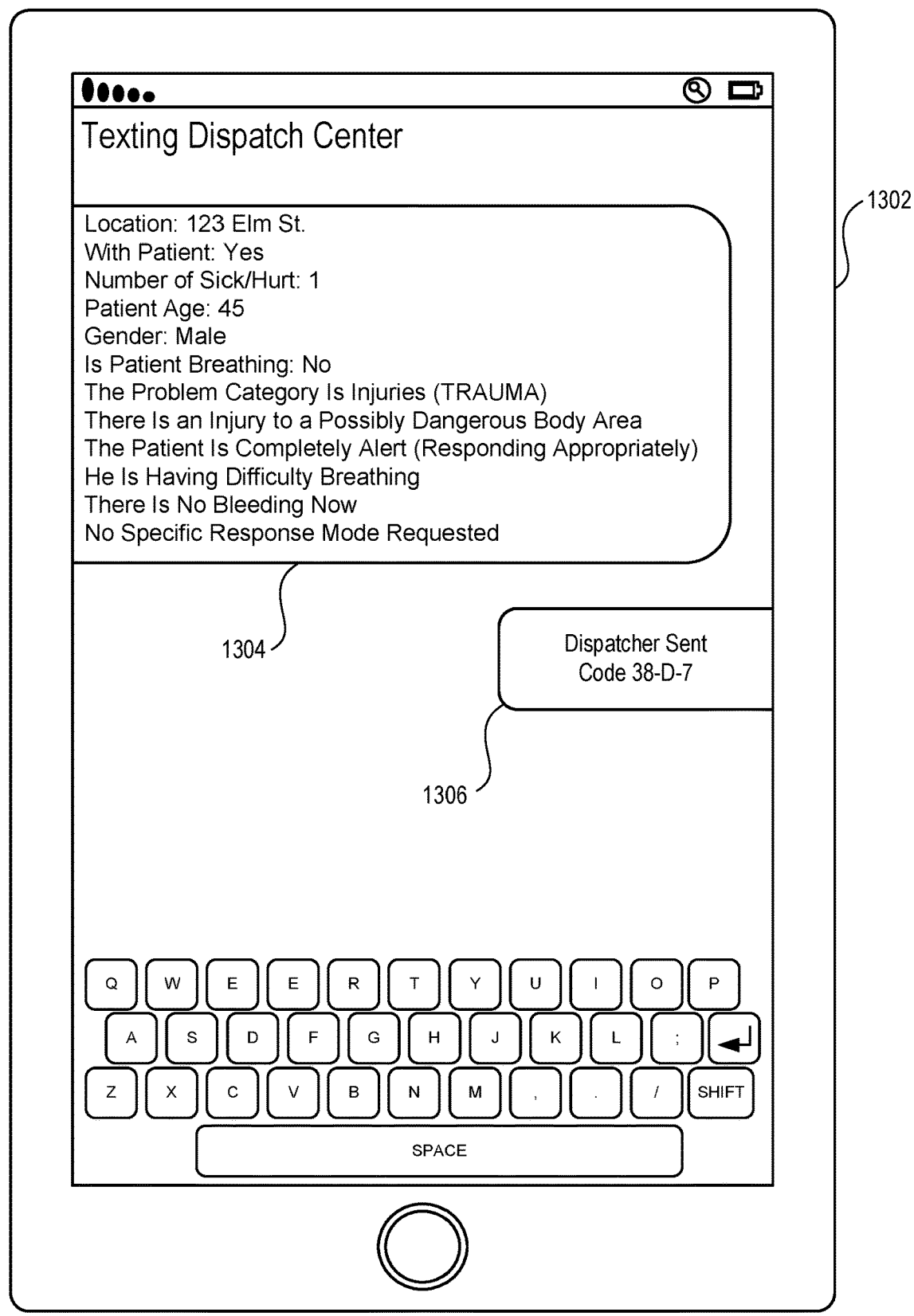
FIG. 13 illustrates an embodiment of a text message for an emergency dispatch protocol.

FIG. 13 illustrates an embodiment of a text message for an emergency dispatch protocol 110. Rather than calling into the dispatch center 102 to verbally relay information to a dispatcher 104 to enter into the computer for use with the case entry protocol 202 and/or the expedited dispatch protocol 210, an information provider 114 may use a cellular phone 1302 to send a first text message 1304 comprising one or more pieces of that information directly to the computer 106 of the dispatch center 102. The cellular phone 1302 may be the phone 136. The cellular phone 1302 may be, but need not be, a smartphone. The first text message 1304 may list one or more items of information needed by the case entry protocol 134 and/or the expedited dispatch protocol 116, as those items of information have been heretofore described. The information provider 114 may be aware of some or all of the items of information useful to a particular path through the case entry protocol 134 and/or the expedited dispatch protocol 116 due to training and/or through the use of information on an outside resource (e.g., the "Advanced SEND" card of FIGS. 11A-11B) to jog their memory. Use of the information found in the first text message 1304 after it is received by the computer 106 of the dispatch center 102 is described further below.

It is further contemplated that rather than sending a text message to the computer 106 of the dispatch center 102, an information provider 114 may instead call the computer 106 and verbally relay needed information for a case entry protocol 134 and/or the expedited dispatch protocol 116 to an automated system of the computer 106. This system may use voice recognition to parse the information that has been so provided. This parsing may occur in real time and/or using a recording of the verbal information from the information provider 114. The computer 106 may then treat this information similarly to the case of information received from a mobile application or text message.

Upon receiving direct information from the information provider 114 (e.g., via the mobile application of FIGS. 12A-12G and/or the text message/voice methods described in relation to FIG. 13), the computer 106 may then activate the determinant code calculator 118 and use it with the received information. Once this is complete, the computer 106 may alert the dispatcher 104 of the new information and/or the new determinant code calculation (e.g., via a noise and/or an on-screen or other visual indication).

It may be that the new information (however received) and the corresponding new determinant code calculation is then displayed to the dispatcher using embodiments of a user interface of the computer 106 as already described herein. Note that both the path through the expedited dispatch protocol 210 taken by the mobile application of FIGS. 12B-12G and the information in the first text message 1304 correspond to the path taken via dispatcher input in FIGS. 3B-3G. In this case, it may then follow that the received information and calculated determinant code are presented to the dispatcher 104 on a user interface of the computer 106 in substantially similar manner as shown in FIG. 3H. The dispatcher 104 would then be free to review the received information in a summary field like that of the summary field 324 in FIG. 3H and confirm the generation of an emergency response corresponding to the calculated determinant code by using a send field like that of the send field 326 in FIG. 3H.

Should the information provider 114 use the user interface 1204 of the software on the smartphone 1202 (or other device) to instead take a different path through the expedited dispatch protocol 210 (or should the provided text message/voice data correspond to a different path through the expedited dispatch protocol 210) than the path described in FIGS. 3B-3G, it is anticipated that the user interface displayed by the computer 106 of the dispatch center 102 for the dispatcher 104 after receiving that new information would be correspondingly different. Examples of other possible displayed results that correspond to different paths taken through the expedited dispatch protocol 210 (and thus potentially different calculated determinant codes) are shown in, e.g., FIGS. 4F, 5E, 6F, 7G, 8D, 9E, and 10F.

Once the dispatcher 104 has confirmed an emergency response to be dispatched (e.g., via communication with the CAD system 120, as described above), a reply may be sent by the computer 106 to the information provider 114 to confirm the dispatch to the information provider 114. This reply may be, e.g., a dialog box in presented in the user interface 1204, a text message response (e.g., the second text message 1306), or a return phone call, among other contemplated methods. The reply may include the determinant code used by the dispatcher 104 as part of the dispatch As disclosed, an expedited dispatch protocol allows a first responder to communicate with a dispatch center 102 and provide patient information with little or no prompting from a dispatcher 104 and receive expedited processing. The expedited dispatch protocol processes the patient information and generates a determinant code which indicates the priority of the emergency. The expedited dispatch protocol provides a uniform, consistent result to objectively select priority and generate an appropriate emergency response. Accordingly, uniform and consistent results are achieved through the disclosed system and variance due to human subjectivity is minimized.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer system to perform a method to assist a dispatcher in responding to an information provider requesting an emergency medical response for a patient of a medical emergency, comprising:
    a processor;
    an input device in electrical communication with the processor;
    an output device in electrical communication with the processor; and
    a memory in electrical communication with the processor, and having stored thereon:
        an expedited dispatch protocol to receive information as pre-scripted inputs provided by the information provider without the dispatcher prompting the information provider, the expedited dispatch protocol to determine a nature of the medical emergency based on the pre-scripted inputs; and
        a determinant calculator to automatically generate a determinant code from one of a plurality of pre-established determinant codes, the determinant code indicating a priority of the emergency medical response based on the information provided by the information provider, the computer system providing, responsive to an input to the computer system from the dispatcher, the determinant code to a computer aided dispatch system to generate an emergency dispatch response.

2. The computer system of claim 1, further including an emergency dispatch protocol comprising the expedited dispatch protocol and an interrogative dispatch protocol, the interrogative dispatch protocol to receive information from the information provider using preprogrammed inquiries for the dispatcher to ask the information provider.

3. The computer system of claim 2, wherein the emergency dispatch protocol is to proceed with the expedited dispatch protocol responsive to an information provider that is identified as a first responder.

4. The computer system of claim 3, wherein the information provider is identified as the first responder through verbal communication with the dispatcher.

5. The computer system of claim 3, wherein the information provider is identified as the first responder through the use of a dedicated information channel.

6. The computer system of claim 2, wherein the emergency dispatch protocol is to proceed with the interrogative dispatch protocol responsive to an information provider that is not identified as a first responder.

7. The computer system of claim 2, the emergency dispatch protocol further comprising a case entry protocol to collect initial information before the emergency dispatch protocol proceeds with another protocol.

8. The computer system of claim 7, wherein the initial information includes a conscious state of the patient.

9. The computer system of claim 8, wherein the initial information includes a patient's age.

10. The computer system of claim 1, wherein the expedited dispatch protocol provides, on a user interface of the computer system, a summary of provided pre-scripted inputs and the determinate code.

11. The computer system of claim 1, wherein the information as pre-scripted inputs is provided by the information provider via a smartphone application.

12. The computer system of claim 1, wherein the information as pre-scripted inputs is provided by the information provider via a text message.

13. A non-transitory computer readable medium comprising computer readable instruction code to perform a method to assist a dispatcher in responding to an information provider requesting an emergency medical response for a patient of a medical emergency, the method comprising:
    receiving pre-scripted inputs from a first responder information provider without the dispatcher prompting the first responder information provider;
    determining a nature of the medical emergency based on the pre-scripted inputs;
    automatically generating a determinant code, from one of a plurality of pre-established determinant codes, the determinant code indicating a priority of the emergency medical response based on the pre-scripted inputs; and
    providing, responsive to an input to a computer from the dispatcher, the determinant code to a computer aided dispatch system to generate an emergency dispatch response.

14. The non-transitory computer readable medium of claim 13, wherein the method further comprises providing, on a user interface, a pre-scripted interrogation comprising a plurality of preprogrammed inquiries for the dispatcher to ask the information provider to systematically obtain a description of the medical emergency, wherein the description of the medical emergency comprises information provider responses to the plurality of preprogrammed inquiries.

15. The non-transitory computer readable medium of claim 13, wherein the method further comprises identifying the information provider as the first responder.

16. The non-transitory computer readable medium of claim 13, wherein the pre-scripted inputs include a main medical problem of the patient.

17. The non-transitory computer readable medium of claim 13, wherein the pre-scripted inputs include an indication that an injury is in a possibly dangerous body area.

18. The non-transitory computer readable medium of claim 13, wherein the pre-scripted inputs include patient chest pains.

19. The non-transitory computer readable medium of claim 13, wherein the pre-scripted inputs include patient bleeding.

20. The non-transitory computer readable medium of claim 13, wherein the pre-scripted inputs include a response mode of the emergency medical response.

21. The non-transitory computer readable medium of claim 13, wherein the method further includes providing to the dispatcher, on a user interface, a summary of entered pre-scripted inputs and the determinate code.

22. The non-transitory computer readable medium of claim 13, wherein the pre-scripted inputs are received from the first responder information provider via a software application of a smartphone of the first responder information provider.

23. The non-transitory computer readable medium of claim 13, wherein the pre-scripted inputs are received from the first responder information provider via a text message from a cellular phone of the first responder information provider.

24. A method for responding to an information provider requesting an emergency medical response for a patient of a medical emergency, the method comprising:

receiving pre-scripted inputs from an information provider without a dispatcher prompting the information provider;
   determining a nature of the medical emergency based on the pre-scripted inputs;
   automatically generating a determinant code, from one of a plurality of pre-established determinant codes, the determinant code indicating a priority of the emergency medical response based on the pre-scripted inputs; and
   providing the determinant code to a computer aided dispatch system to generate an emergency dispatch response.

25. The method of claim 24, wherein the pre-scripted inputs from an information provider are received via a smartphone application.

26. The method of claim 24, wherein the pre-scripted inputs from an information provider are received via a text message.

* * * * *